US012434025B1

(12) United States Patent
Luo

(10) Patent No.: US 12,434,025 B1
(45) Date of Patent: Oct. 7, 2025

(54) RESPIRATORY DEVICE WITH A CONTAINMENT CHAMBER

(71) Applicant: WALLENBERG UNION LLC, Newark, DE (US)

(72) Inventor: David Luo, Newark, DE (US)

(73) Assignee: WALLENBERG UNION LLC, Newark, DE (US)

( * ) Notice: Subject to any disclaimer, the term of this patent is extended or adjusted under 35 U.S.C. 154(b) by 0 days.

(21) Appl. No.: 18/785,985

(22) Filed: Jul. 26, 2024

(51) Int. Cl.
*A61M 16/00* (2006.01)

(52) U.S. Cl.
CPC .... *A61M 16/0066* (2013.01); *A61M 16/0003* (2014.02); *A61M 2202/0007* (2013.01); *A61M 2202/02* (2013.01); *A61M 2205/103* (2013.01); *A61M 2205/42* (2013.01)

(58) Field of Classification Search
CPC .............. A61M 16/00; A61M 16/0003; A61M 16/0066; A61M 16/0069; A61M 16/022; A61M 2016/0027; A61M 2016/003; A61M 2205/3334; A61M 2205/3344; A61M 2205/3368; A61M 2205/3606; A61M 2205/362; A61M 2205/42; A61M 2205/502; A61M 2205/583; F04B 53/003; F04D 25/08; F04D 25/082; F04D 27/00; F04D 27/001; F04D 27/004; F04D 29/5806; F04D 29/584; F04D 29/626; F04D 29/664; F04D 29/668; F05D 2270/3015; Y02B 30/70
See application file for complete search history.

(56) References Cited

U.S. PATENT DOCUMENTS

| | | | | |
|---|---|---|---|---|
| 7,617,823 | B2 * | 11/2009 | DiMatteo | F04D 29/664 128/204.21 |
| 11,491,290 | B2 * | 11/2022 | Higashiyama | A61M 16/00 |
| 2008/0257346 | A1 * | 10/2008 | Lathrop | A61M 16/0066 181/224 |
| 2014/0014109 | A1 * | 1/2014 | Grasmuck | A61M 16/0066 128/204.18 |

* cited by examiner

*Primary Examiner* — Annette Dixon
(74) *Attorney, Agent, or Firm* — HSML P.C.

(57) ABSTRACT

A respiratory device with a containment chamber, configured to deliver pressurized breathable gas to a patient's airway, including a blower configured to generate pressurized breathable gas, a gas passage with at least two chambers, and a casing that houses the gas passage. At least one of the at least two chambers is a containment chamber, the other chambers are at least one flow chamber. The containment chamber communicates with the at least one flow chamber through a neck. When the respiratory device is in use, the airflow substantially does not pass through the containment chamber; the neck is only configured to communicate with the chambers and allows minimal or no airflow through it. Noise enters the containment chamber through the neck and dissipates by resonating with the walls of the chambers, achieving maximal noise reduction for the respiratory device.

19 Claims, 24 Drawing Sheets

RESPIRATORY DEVICE WITH A CONTAINMENT CHAMBER

TECHNICAL FIELD

This disclosure pertains to a device used to improve or treat respiratory system-related disorders, such as sleep apnea, including at least one blower and a gas passage with at least two chambers.

BACKGROUND

Good sleep is crucial for physical endurance and energy recovery. Obstructive Sleep Apnea Hypopnea Syndrome (OSAHS), commonly known as snoring, is one of the most common sleep disorders that significantly endangers human health. It involves the excessive relaxation of the muscles at the back of the throat, which leads to breathing difficulties. These muscles support the rear of the roof of the mouth (soft palate), the tongue, and the lateral pharyngeal walls. When these muscles relax, the airway narrows or closes during inhalation, reducing oxygen levels in the blood. The brain, sensing breathing difficulties, prompts brief awakenings to reopen the airway. Alternatively, symptoms might include nasal congestion, choking, or loud gasping. Depending on the severity of the condition, this sleep breathing pattern can repeat 5 to 30 times per hour, or a sleep apnea hypopnea index (AHI) of at least five per hour, accompanied by symptoms like excessive daytime sleepiness, thereby disrupting the patient's ability to reach deep sleep stages, leading to insufficient sleep and drowsiness during the day. Given the severe impact of sleep disorders, diagnosing and timely treatment are essential to protect the patient's physical and mental health.

For mild cases of sleep apnea, symptoms can be alleviated by lifestyle changes such as weight loss, smoking cessation, and altering sleep positions. For moderate to severe cases, medical devices are necessary to open the blocked airways; in more severe cases, surgery may be required.

Among medical treatment methods, Continuous Positive Airway Pressure (CPAP) therapy is the most effective non-surgical treatment for OSAHS. One type of positive pressure breathing device is the Continuous Positive Airway Pressure (CPAP) device, which is a pump that increases airway pressure during sleep. It delivers a continuous positive airflow through a mask into the airway, maintaining the airway open throughout the breathing cycle by keeping it under positive pressure. CPAP devices are available in either fixed or auto-adjusting models. Another type is the Bilevel Positive Airway Pressure (BiPAP) device, also a non-invasive ventilation device, which allows for separate settings of inspiratory positive airway pressure (IPAP) and expiratory positive airway pressure (EPAP). PAP therapy improves the Epworth Sleepiness Scale scores in patients with OSAS, reduces AHI and arousal index, and enhances the lowest nighttime oxygen saturation. It can alleviate snoring and breath-holding during sleep, improve or eliminate daytime sleepiness, and ameliorate or eliminate other accompanying symptoms and complications. However, approximately 30% to 50% of PAP users cite noise as a problem with using PAP therapy, indicating that noise issues do impact people's willingness to use CPAP therapy. Therefore, optimizing the noise levels of PAP ventilators could potentially increase patient acceptance of PAP treatment.

Noise sources in PAP ventilators can be categorized into the following: the blower, airflow, leaks, vibrations, and structure. The blower, provided within the ventilator's gas passage, produces noise from airflow and vibrations, which are closely related to the internal structure of the gas passage and the assembly of the blower within the gas passage. Currently, ventilators on the market generally utilize internal soundproofing materials to achieve better noise reduction. Due to their unique porous structure and material properties, these soundproofing materials can convert noise into minite amounts of energy, effectively reducing noise. However, as the soundproofing materials are constantly exposed to a high-pressure, high-velocity, and high-vibration environment, their physical structure can degrade over time due to friction or compression. This degradation can lead to the breaking of connections between the pores of the material, resulting in small particles or fragments detaching and entering the patient's airway with the high-velocity gas, which can be harmful to human health over long-term use.

SUMMARY

The objective of this disclosure is to provide a respiratory device that is safer, quieter and more reliable.

In one embodiment, a respiratory device with a containment chamber is provided. The respiratory device includes at least one blower, a gas passage, a casing, and an electronic assembly. The at least one blower includes a motor with a rotor, at least one impeller on the rotor, and a housing with an inlet and an outlet. The at least one blower is configured to generate pressurized breathable gas. The gas passage includes walls with an air intake and an air outlet. The walls are configured to form at least two chambers. The casing is configured to house the gas passage, and the electronic assembly is provided between the casing and the gas passage. At least one of these chambers is the containment chamber. The containment chamber includes at least one wall with at least one through-opening, and when the respiratory device is in use, breathable gas substantially does not pass through the containment chamber.

In one embodiment, the at least two chambers, other than the containment chamber, include at least one flow chamber. The at least one blower is provided on one or more of the at least one flow chamber.

In one embodiment, one or more of the at least one wall of the containment chamber is flat.

In one embodiment, one or more of the at least one wall of the containment chamber is curved.

In one embodiment, a volume of airflow through one of the containment chamber accounts for at most 20% of the total volume of the airflow through the respiratory device.

In one embodiment, the at least one through-opening on the containment chamber takes the form of a circle with a diameter of at least 0.5 mm.

In another embodiment, a respiratory device with a containment chamber is provided. The respiratory device includes at least one blower, a gas passage, a casing, and an electronic assembly. The at least one blower includes a motor with a rotor, at least one impeller on the rotor, and a housing with an inlet and an outlet. The at least one blower is configured to generate pressurized breathable gas. The gas passage includes walls with an air intake and an air outlet, and the walls are configured to form at least two chambers. The casing is configured to house the gas passage, and the electronic assembly is provided between the casing and the gas passage. At least one of these chambers is the containment chamber and the at least two chambers other than the containment chamber are at least one flow chamber. The containment chamber includes at least one wall with at least one through-opening. Aside from the at least one wall with the at least one through-opening, the other walls of the containment chamber are closed. The at least one through-opening of the containment chamber communicates with the at least one flow chamber through a neck.

In one embodiment, the at least one blower is provided within one or more of the at least one flow chamber.

In one embodiment, the height of the neck is at least 0.4 mm.

In one embodiment, a volume of airflow through one of the containment chamber accounts for at most 20% of the total volume of the airflow through the respiratory device.

In one embodiment, the area of the at least one through-opening on the containment chamber is at least 0.19625 $mm^2$.

In yet another embodiment, a respiratory device with a containment chamber is provided. The respiratory device with a containment chamber includes at least one blower, a gas passage, a casing, and an electronic assembly. The at least one blower includes a motor with a rotor, at least one impeller provided on the rotor, and a housing with an inlet and an outlet. The at least one blower is configured to generate pressurized breathable gas. The gas passage includes walls with an air intake and an air outlet. The walls are configured to form at least two chambers. The casing is configured to house the gas passage, and the electronic assembly is provided between the casing and the gas passage. At least one of these chambers is the containment chamber. The at least two chambers other than the containment chamber are at least one flow chamber. The containment chamber includes at least one wall with at least one through-opening. The at least one through-opening of the containment chamber communicates with the at least one flow chamber through a neck. A maximum cross-sectional area of the neck is at least 0.19625 $mm^2$, and a height of the neck is at least equal to a thickness of the at least one wall of the containment chamber.

In one embodiment, the gas passage includes multiple containment chambers.

In one embodiment, a ratio of the height of the neck to a height of the containment chamber is at least 1:300.

In one embodiment, a maximum cross-section of the neck includes irregular shapes.

In one embodiment, a wall thickness of the containment chamber is at least 0.4 mm.

In a further embodiment, a respiratory device with a containment chamber is provided. The respiratory device with a containment chamber includes at least one blower, a gas passage, a casing, and an electronic assembly. The at least one blower includes a motor with a rotor, at least one impeller provided on the rotor, and a housing with an inlet and an outlet. The at least one blower is configured to generate pressurized breathable gas. The gas passage includes walls with an air intake and an air outlet. The walls are configured to form at least two chambers. The casing is configured to house the gas passage, and the electronic assembly is provided between the casing and the gas passage. At least one of these chambers is the containment chamber. The at least two chambers other than the containment chamber are at least one flow chamber. The containment chamber includes at least one wall with at least one through-opening. The total volume of the containment chamber is at least 785 $mm^2$.

In one embodiment, the gas passage includes multiple containment chambers.

In one embodiment, the containment chamber communicates with the at least one flow chamber through a neck.

In one embodiment, a height of the neck is at least 0.4 mm.

In one embodiment, the surface area of the containment chamber is at most 1000 times the cross-sectional area of the neck.

The implementation of a respiratory device assembly at least includes the following benefits:

1. The containment chamber provided by this disclosure effectively reduces the noise of the device. a. Location: In use, respiratory devices encounter noise due to the opposing directions of the exhaled air from the user and the airflow generated by the blower, or when part of the airflow collides with and changes direction upon hitting the walls of the gas passage, causing some noise to flow out through the air inlet of the gas passage. To mitigate such noise, based on the principles of sound fluctuation and propagation, containment chambers are added at noise concentration areas such as the air intake of the gas passage and the inlet of the blower. These chambers capture and dissipate noise through vibration. Depending on the placement of the containment chamber and applying aerodynamic principles, different noise reduction effects can be achieved. For example, a containment chamber provided at the blower inlet leverages the principle of negative pressure in aerodynamics. The high-speed airflow at the opening creates negative pressure inside the containment chamber, slowing down the noise propagation due to reduced transmission medium, decreasing the likelihood of sound reflection and allowing the noise retained in the containment chamber to dissipate through vibrations against the chamber walls. b. Principle: While the wall of the containment chamber connected to the neck includes an opening, the other walls of the containment chamber are closed (i.e., without openings), and the area of the opening is proportionate to the surface area of the containment chamber, effectively reducing noise escape from the opening. The centerline of the neck is oriented at an angle greater than 30° relative to the main airflow path to ensure noise enters the containment chamber while preventing excessive airflow from entering, allowing the noise within the containment chamber to convert sound energy into kinetic energy through vibration. c. Material: The primary function of the containment chamber is to convert sound energy into other forms of energy. The containment chamber includes rigid materials that resonate with the noise's sound waves against the walls of the containment chamber, thus converting sound energy into kinetic energy to silence the noise. Alternatively, the containment chamber can include materials such as silicone, where the noise's sound waves, passing through these materials, are converted into thermal energy through friction and vibration, thereby reducing or eliminating noise.

2. The containment chamber can replace the soundproofing materials in respiratory devices, enhancing the safety of the devices. The design of a gas passage without soundproofing materials improves the safety of the devices. In 2021, a renowned international brand issued its first global recall notice involving some of its BiPAP devices, CPAP devices, and mechanical ventilators, followed by several more recalls. The recalls were primarily due to the use of sound-dampening materials within the gas passages of the ventilators, which could release particles and volatile organic compounds. The FDA received numerous complaints about this brand's CPAP and BiPAP ventilators. This incident not only had a negative impact on the brand but also affected millions of its users. Ventilators must achieve a noise level of 30 dB or less for marketing approval in FDA's regulations, and using soundproofing materials for noise reduction is currently the simplest method. Soundproofing materials, due to their unique porous structure and material properties, can convert noise into small amounts of energy to achieve effective noise reduction. Placing soundproofing materials inside the gas passage is the simplest and most common way to meet regulatory noise levels. However, soundproofing materials can easily cause health problems for several reasons: a. Soundproofing materials are typically made from synthetic materials such as polyurethane and polyether, which often contain various chemical additives or components. During the use of the device, these additives or components may gradually be released and turn into harmful substances that are detrimental to human health. Prolonged inhalation of these substances can negatively impact respiratory health and overall well-being. b. Soundproofing materials are often hygroscopic, which can be problematic in the humid environments created by ventilators during operation. These materials absorb moisture from the air, creating ideal conditions for the growth of bacteria and mold. Additionally, some ventilators provide humidification systems to enhance patient comfort, further promoting moisture absorption in the soundproofing materials within the internal environment. c. When the gas passage is in operation, airflow moves through the soundproofing materials, causing friction and vibration. This can lead to the deterioration of the material surface and the release of tiny particles. The hygroscopic nature of the soundproofing materials not only fosters bacterial or fungal growth but can also lead to the decomposition of the material itself, generating small particles. These particles can ultimately be inhaled into the patient's respiratory system, posing significant health risks. Some patients may also have allergic reactions to these materials, potentially leading to respiratory allergic reactions or asthma attacks, thereby impacting respiratory health. These factors typically shorten the lifespan of soundproofing materials, necessitating frequent replacement to maintain their effectiveness in the gas passage. Alternatively, further research and development to enhance the physical and chemical stability of these materials can be pursued, though this would increase the costs associated with usage and production.

The noise reduction structure provided by this disclosure can achieve regulatory noise levels within the gas passage with reduced use of soundproofing materials, thus enhancing both the safety and the lifespan of the device, as well as aligning with environmental sustainability principles compared with the existing ventilator's design with foam within the gas passage. The noise reduction structure provided by this disclosure incorporates a series of improvements and uses multiple effective noise-reducing structures, supported by theoretical and experimental data. The resulting gas passage significantly reduces noise, meeting regulatory noise levels without the use of soundproofing materials. The advantages of reducing soundproofing materials in the gas passage at least include: a. Placing soundproofing materials within the gas passage is the most straightforward and common method to achieve regulatory noise levels in devices related to respiratory care. However, particles from the decomposition of these materials, if inhaled, are usually harmful to human health, particularly for those requiring long-term and prolonged use of ventilators. b. Soundproofing materials degrade and damage quickly compared to plastic materials and are among the shortest-lived components used within the gas passage. The lifespan of gas passages containing soundproofing materials is reduced due to the presence of these materials. This disclosure allows patients to opt for a gas passage with reduced soundproofing materials, thereby enhancing the overall lifespan of the ventilator. Additionally, the absence of soundproofing materials means a simpler internal structure of the gas passage, eliminating the need for extra fixtures to secure these materials, reducing mechanical wear and maintenance requirements, and improving the device's reliability and stability. c. While soundproofing materials are a common means of noise reduction in ventilators and effectively lower noise levels, their manufacture, use, and disposal have environmental impacts. Firstly, as synthetic materials, their production requires significant energy and resources, and may involve the use of chemicals that contribute to pollution. Besides, high-quality noise-reducing soundproofing materials are generally costly, reducing health risks but also increasing the purchase costs of the devices. Designs that reduce soundproofing materials within the gas passage avoid these issues. They not only lessen the environmental impact but also reduce waste production and save costs associated with purchasing these materials. d. Gas passages with reduced soundproofing materials which meet regulatory noise levels provide patients with more flexible options. Patients can choose between gas passages with or without soundproofing materials. Those with higher requirements for quietness may opt for passages with soundproofing materials to achieve lower noise levels and improve sleep quality. Alternatively, adding health-friendly materials like silicone or rubber within the gas passage can also reduce noise while eliminating the impacts of soundproofing materials. Compared to soundproofing materials, silicone and plastics usually offer better durability, corrosion resistance, and resilience, are less affected by environmental conditions, and have better chemical stability, making them less susceptible to chemical influences and thus longer-lasting.

By utilizing effective noise reduction structures such as the containment chamber, the respiratory device can achieve the regulatory or even lower noise levels without relying on materials prone to decomposition or degradation, ensuring greater stability. This disclosure uses multiple structures that effectively reduce noise, offering an alternative to traditional gas passages that utilize soundproofing materials. Specifically, the various noise reduction structures employed in this disclosure include, but are not limited to, the containment chamber, the conical inlet tube, more strategically placed and positioned blowers, arc-shaped walls that are essentially coaxial with the inlet of the blower intake, and inner walls with rounded contours of the gas passage that are positioned opposite the airflow path. The use of these structures and components not only lowers the noise level of the device but, more importantly, the noise-reducing components within the gas passage and the internal structure of the gas passage itself, as well as the positional relationships among various structures, are all based on ample existing and experimental data supported by scientific analysis. This ensures the scientific validity and credibility of the design of the gas passage, which makes the gas passage's performance more reliable and stable. This gas passage design not only improves the performance of the product but also provides patients with a quieter and more reliable user experience.

3. The structural design of the containment chamber enhances the device's reliability and extends its operational lifespan. The gas passage design, free from materials prone to decomposition or degradation, utilizes physically and chemically stable structures to prolong the device's lifespan, ensuring longer-lasting use. Additionally, the design eliminates the need for easily degradable materials, simplifying the internal structure of the gas passage. This obviates the need for extra components to secure special materials, reducing the variety of production components and thereby lowering the complexity of manufacturing and assembly. This contributes to the device's enhanced reliability and stability. Furthermore, soundproofing materials often require timely replacement and cleaning to ensure health safety, and those placed within devices are typically non-replaceable and non-cleanable. The design without soundproofing materials avoids these maintenance steps, reducing the upkeep required for the internal soundproofing materials of the gas passage and bringing convenience to the maintenance of the device. These aspects make respiratory devices provided by this disclosure more competitive on the market, making them more readily accepted.

4. By employing simpler structures and materials, the respiratory device provided by this disclosure reduces the cost while being environmentally friendly. The gas passage in this disclosure avoids traditional soundproofing materials, thereby reducing the additional costs associated with purchasing and manufacturing soundproofing materials. The gas passage in this disclosure only has plastic parts for the casing of the gas passage and as the material forming the chambers and gas passage, and it uses silicone materials in connectors to secure the blower to the casing of the gas passage. Compared to the more complex structures in the market that include soundproofing materials within the respiratory device's gas passage, this design, composed of only two types of materials, is easier to process and assemble. This simplification makes the manufacturing process more straightforward and efficient, saving substantial time and labor resources. Furthermore, high-quality noise-reducing materials are typically expensive, adding extra cost burdens. In contrast, the design without soundproofing materials lowers these costs. Additionally, reducing the use of auxiliary materials like soundproofing materials also lessens environmental impact, aligning with modern societal demands for environmental sustainability and contributing positively to environmental protection. Soundproofing materials can release harmful chemicals during production and disposal, causing environmental pollution. The gas passage design without these materials avoids the release of such harmful substances, minimizing negative environmental impacts. Therefore, this design, which does not use soundproofing materials or materials prone to decomposition or degradation and relies only on silicone and plastic, not only reduces the cost of the device but also is environmentally friendly, offering a more sustainable and economical solution.

DETAILED DESCRIPTION

Figure 1:
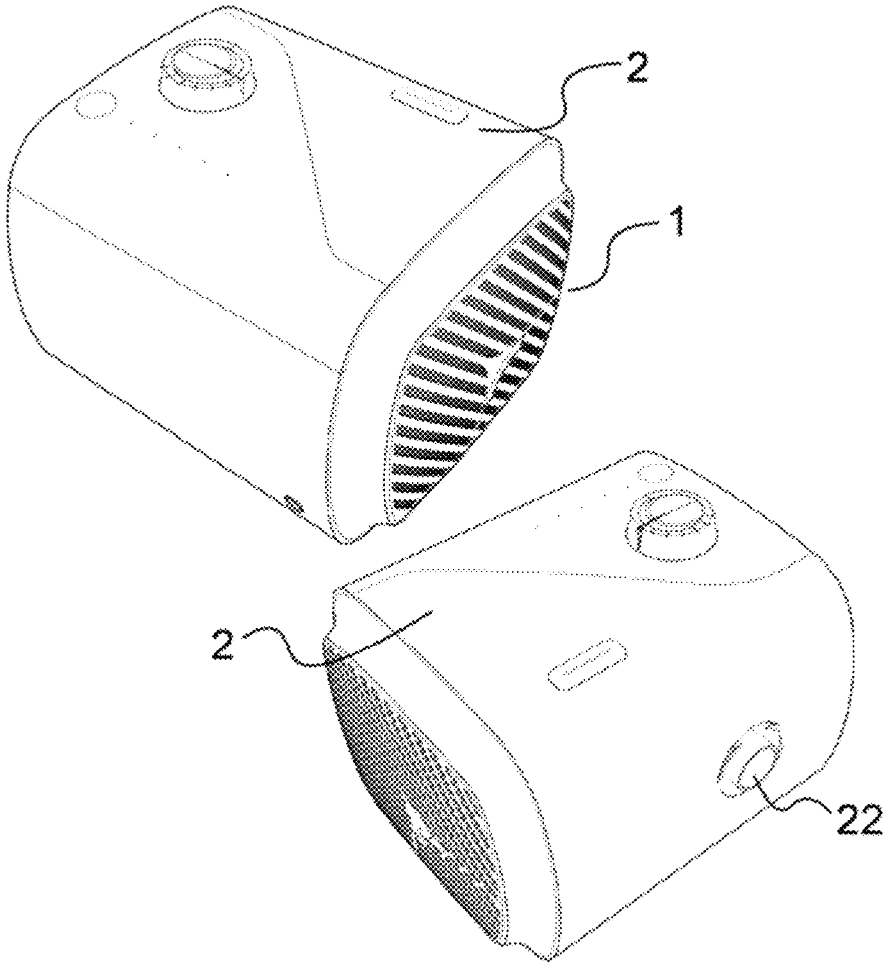
FIG. 1 is a three-dimensional schematic diagram of a respiratory device in accordance with one embodiment.

To make the objectives, features, and advantages of this disclosure more clear and understandable, some specific embodiments of the disclosure are described in detail with reference to the relevant drawings. The descriptions below may include many specific details to provide a comprehensive understanding of the disclosure. However, it must be noted that the disclosure can be implemented in different ways than those described herein. Those of ordinary skill in the art can make similar modifications without departing from the spirit of the disclosure, and thus, the disclosure is not limited by the specific embodiments below.

Detailed embodiments are presented below to elucidate the configurations of the respiratory device provided by this disclosure.

Clarifications for terms used in the embodiments are as follows:

"Substantially", "approximately", "essentially", and "about": In some forms of this disclosure, these terms indicate a variation within fifteen percent of the original value.

"Air" and "gas": In some forms of this disclosure, these terms may refer to the breathable air in everyday life, and in other forms, they may refer to other gases or mixture of gases suitable for breathing, such as atmospheric air enriched with more oxygen.

"Environment": In some forms of this disclosure, "environment" may refer to the area outside of the casing of the gas passage, and in other forms, it may refer to the surroundings in which the patient is located.

Embodiment 1

This disclosure pertains to a respiratory device 1 with a containment chamber, configured to deliver pressurized breathable gas to a patient's airway. The respiratory device 1 includes a blower 3 that continuously generates a positive pressure airflow, a gas passage 4 that regulates and directs the gas, and a casing 2 that houses the gas passage 4. This disclosure, based on the principles of sound propagation, incorporates a closed containment chamber 41 at the noise concentration areas to capture noise. The noise is propagated in a medium where the flow is slow or in a relatively stationary medium, and it resonates with the walls 412 of the containment chamber 41 to effectively cancel out the noise, achieving safe noise reduction. As shown in FIGS. 1, and 3-20, the respiratory device 1 specifically includes at least one blower 3, configured to generate pressurized breathable gas. The blower 3 includes a motor 31 with a rotor 311, at least one impeller 32 provided on the rotor 311, and a housing 33 with an inlet 331 and an outlet 332. The cross-sections of the inlet 331 and outlet 332 of the housing 33 of the blower 3 can be circular, elliptical, square, etc., and they may take the form of an opening or be defined as channels with certain heights. The centerlines of the inlet 331 and outlet 332 of the housing 33 of the blower 3 can be at any angle to each other, such as parallel (as in an axial configuration) or perpendicular (as in a centrifugal configuration). The material of the housing 33 of the blower 3 can include one or more medical-grade materials such as polypropylene, polycarbonate, polyethylene terephthalate-1,4-cyclohexane dimethanol ester, polyamide, polyetheretherketone, silicone, rubber, thermoplastic elastomer, thermoplastic polyurethane, or fluororubber.

Figure 10A:
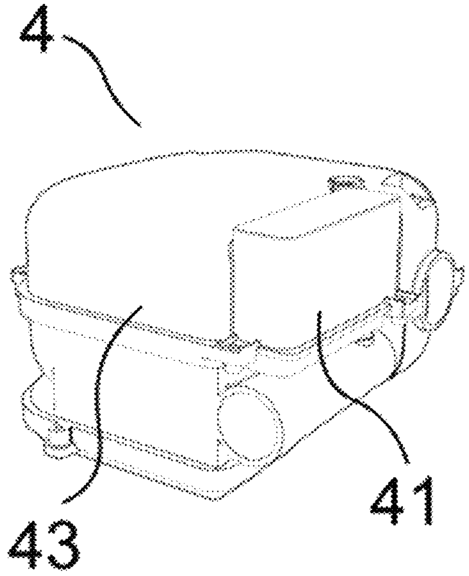
FIGS. 10A and 10B are schematic diagrams of different forms of the containment chamber in the gas passage of a respiratory device in accordance with one embodiment.
Figure 10B:
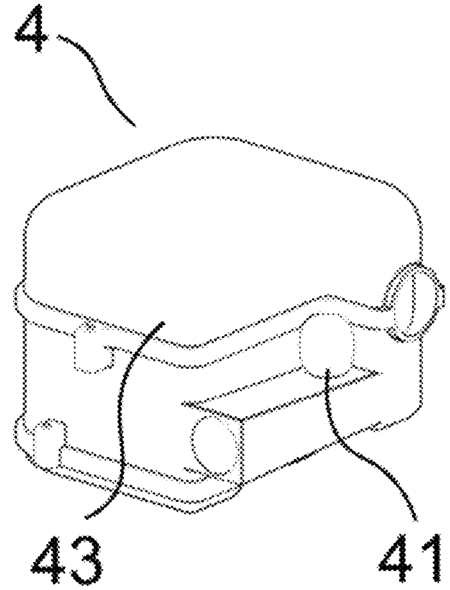
Figure 11:
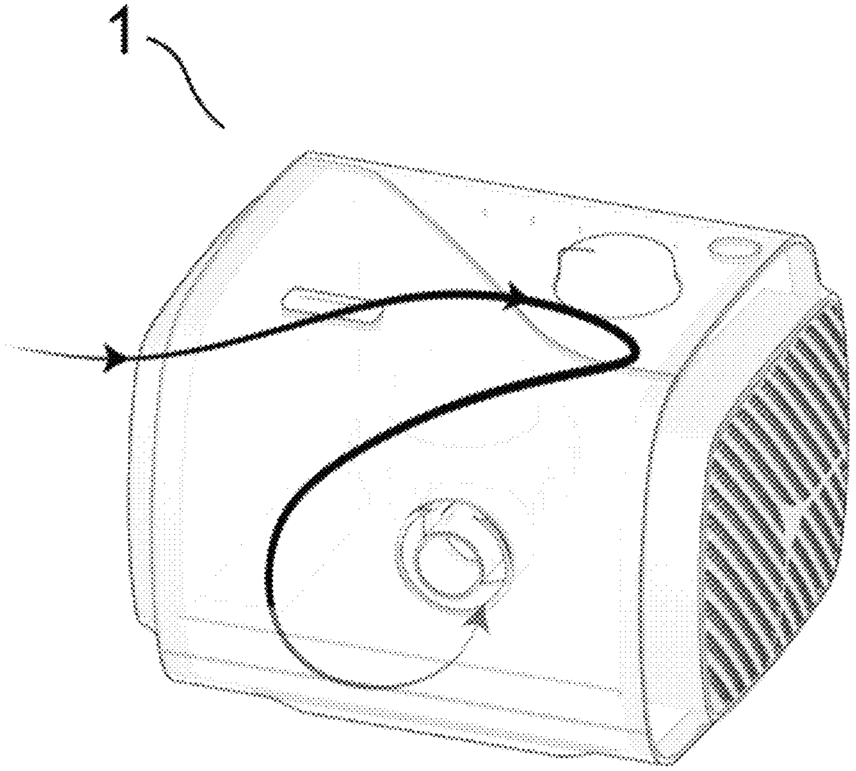
FIG. 11 is a schematic diagram of the spatial arrangement of the airflow path in the gas passage of a respiratory device in accordance with one embodiment.
Figure 12:
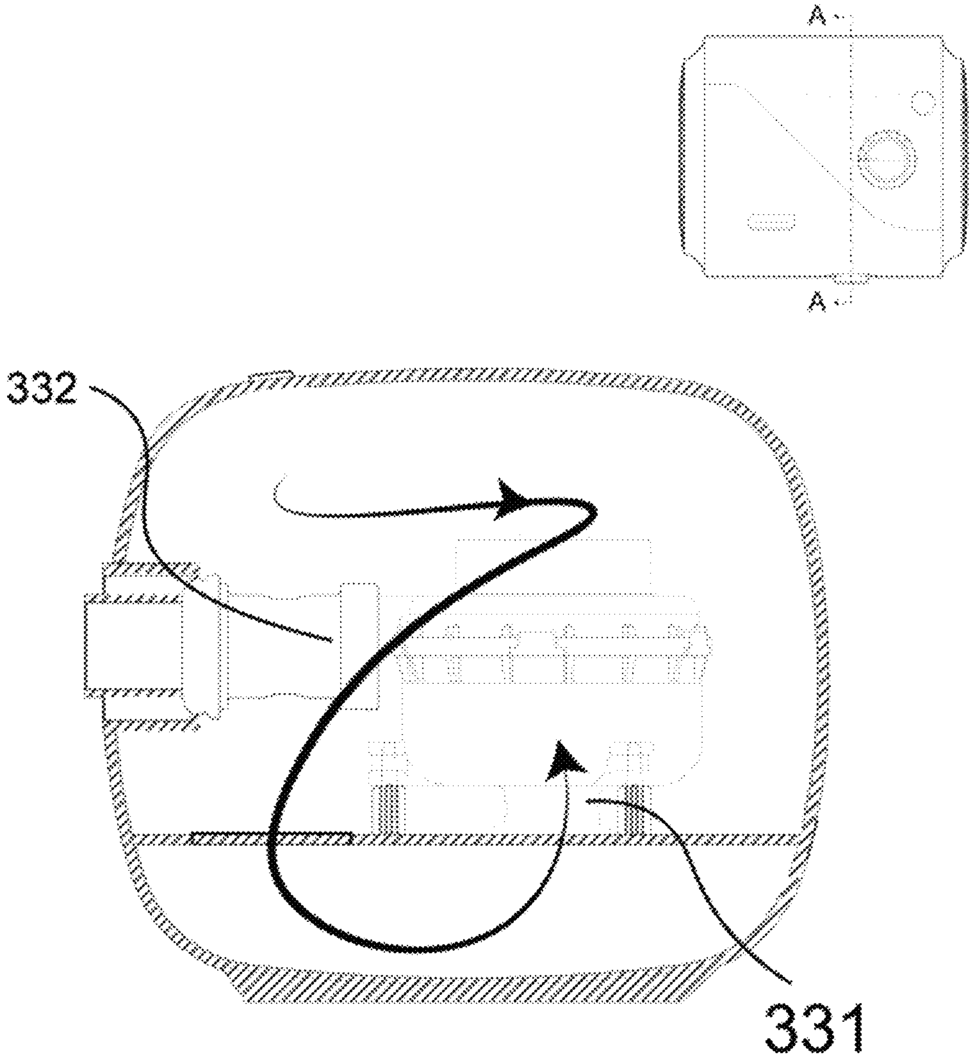
FIG. 12 is a cross-sectional schematic diagram of the airflow path in the gas passage of a respiratory device along line A-A in accordance with one embodiment.
Figure 13A:
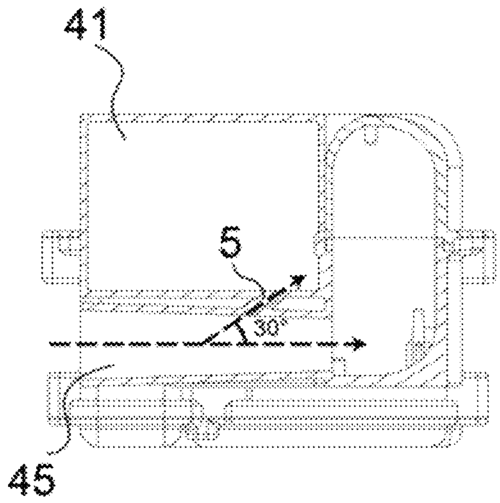
FIGS. 13A, 13B and 13C are schematic diagrams showing the angle between the centerline of the neck and the main airflow path in the gas passage of a respiratory device in accordance with one embodiment.
Figure 13B:
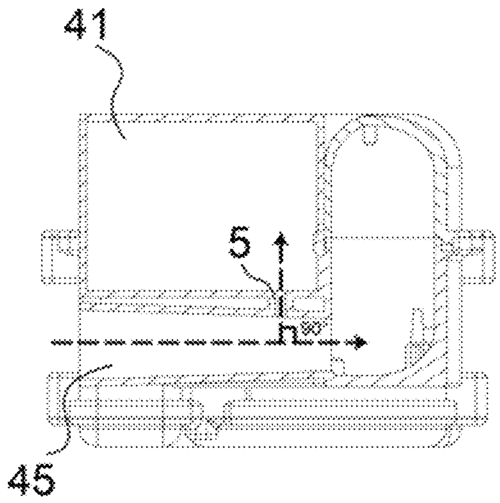
Figure 13C:
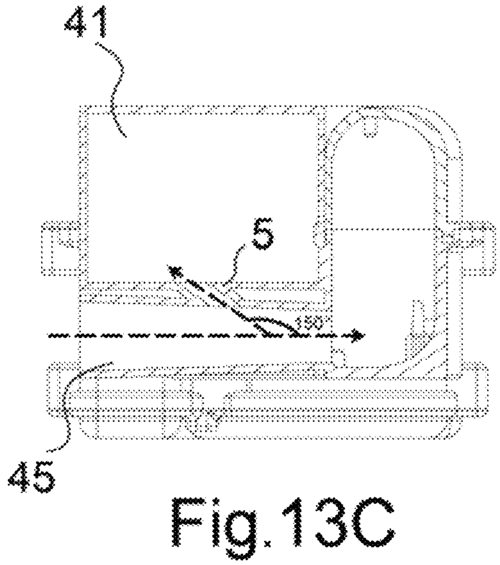
Figure 14:
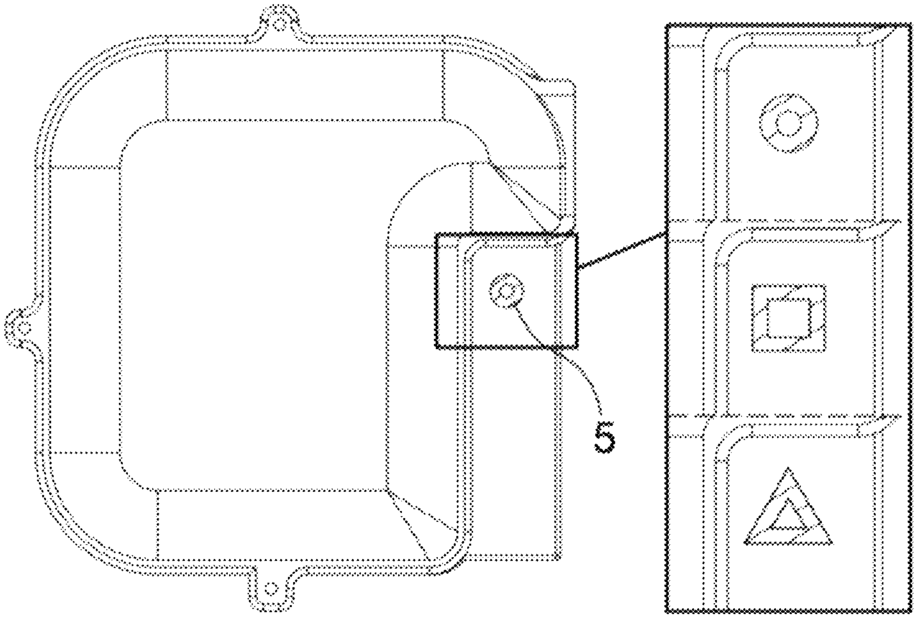
FIG. 14 is a schematic diagram of the cross-sectional form of the neck in a respiratory device in accordance with one embodiment.
Figure 15A:
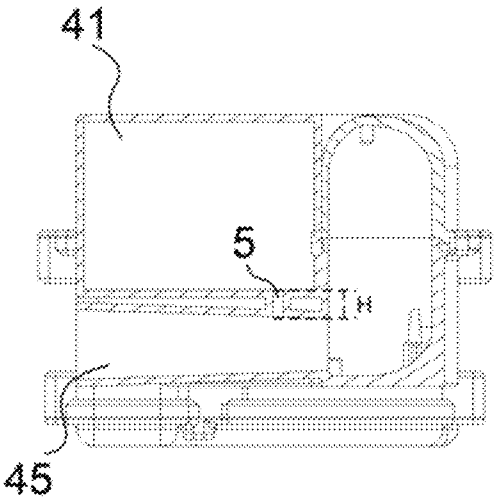
FIGS. 15A and 15B are schematic diagrams showing the height of the neck in the gas passage of a respiratory device in accordance with one embodiment.
Figure 15B:
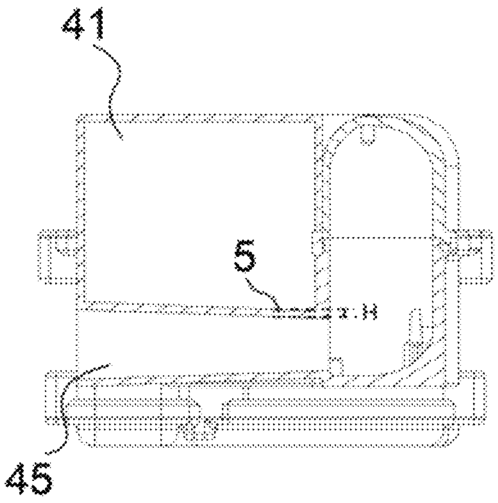
Figure 16:
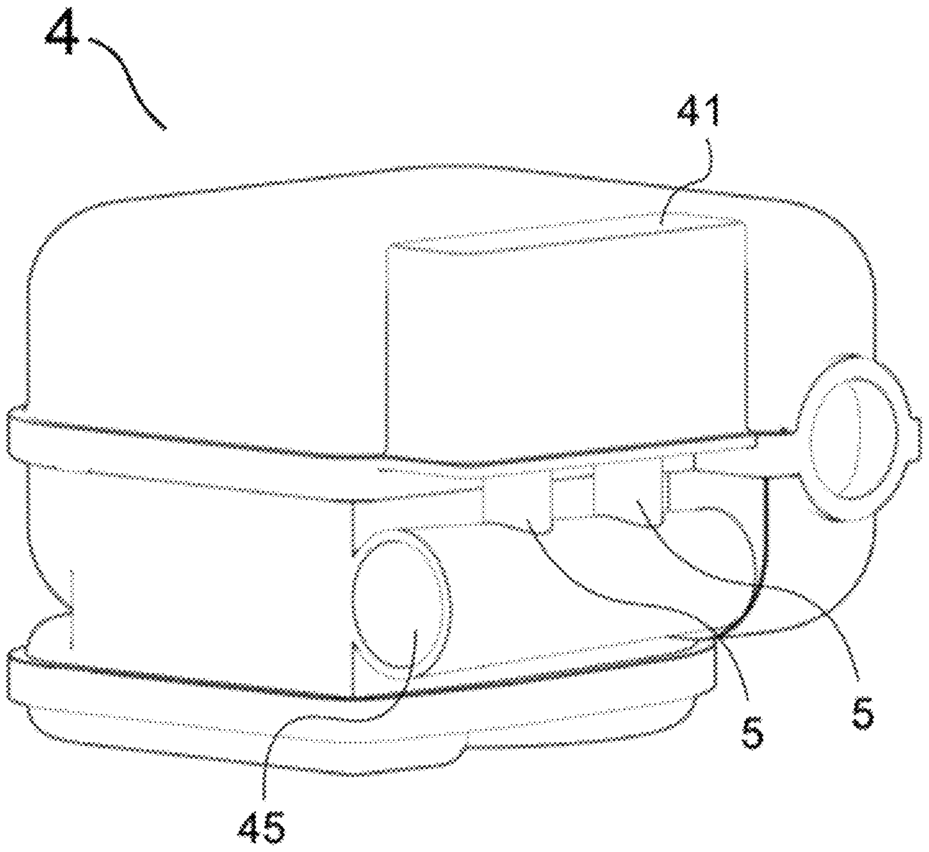
FIG. 16 is a schematic diagram of a wall of the containment chamber with multiple necks in the gas passage of a respiratory device in accordance with one embodiment.
Figure 17:
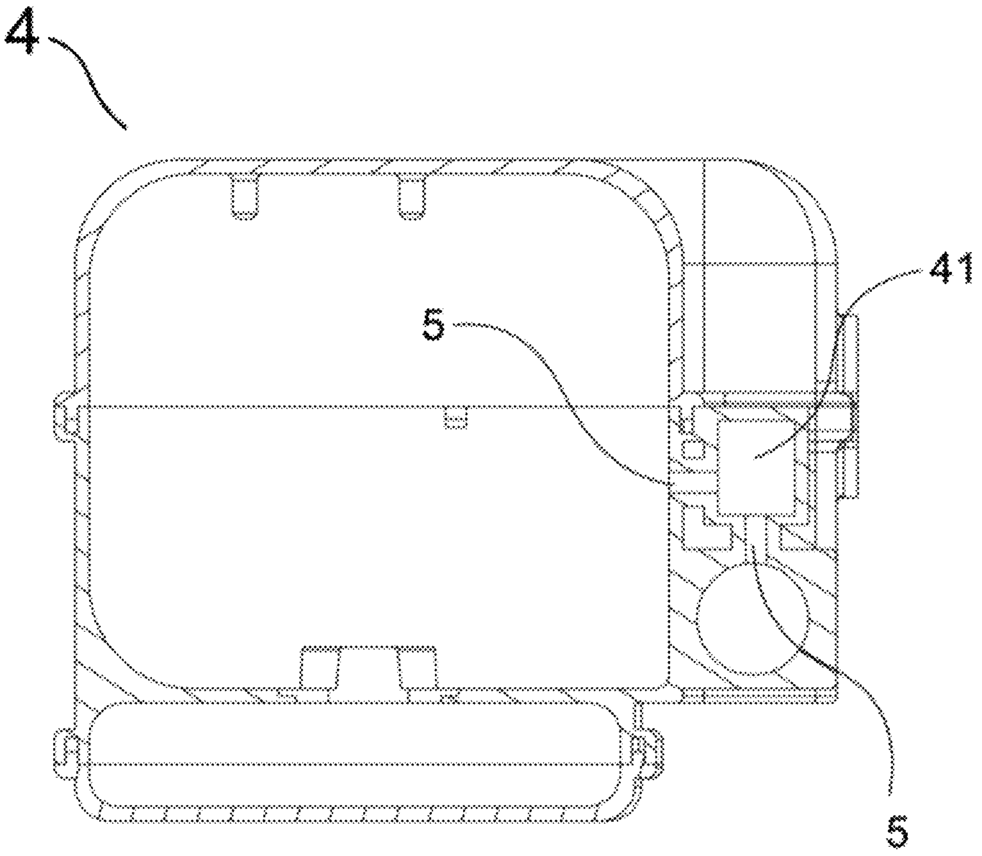
FIG. 17 is a cross-sectional schematic diagram of several walls of the containment chamber having multiple necks in the gas passage of a respiratory device in accordance with one embodiment.
Figure 18:
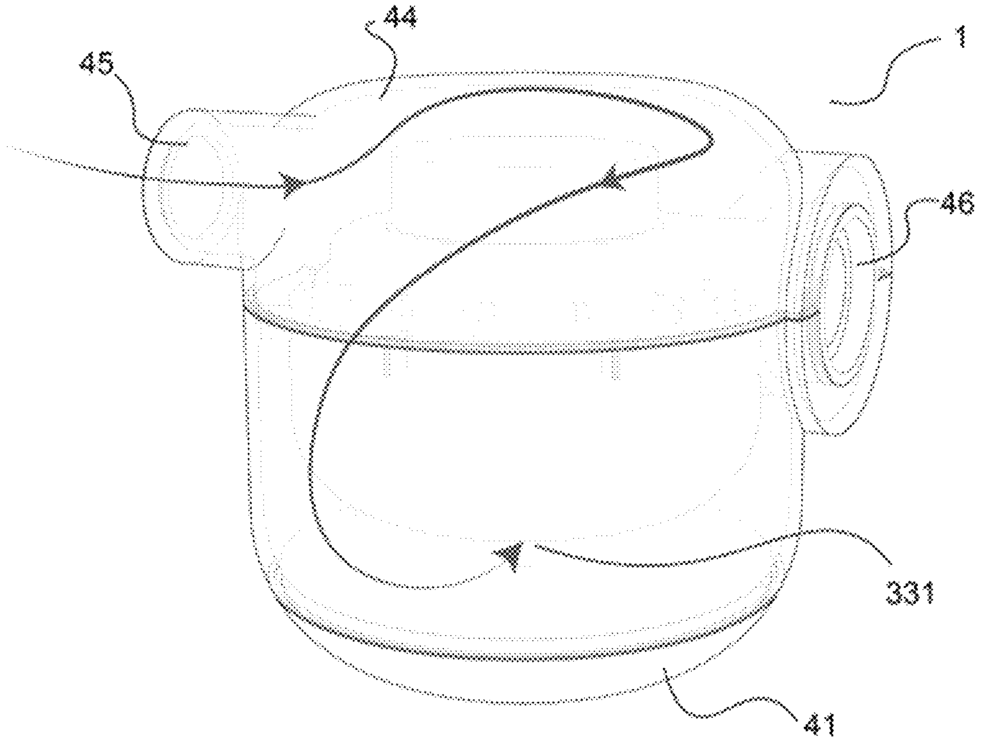
FIG. 18 is a schematic diagram of another form of gas passage in a respiratory device in accordance with one embodiment.
Figure 19:
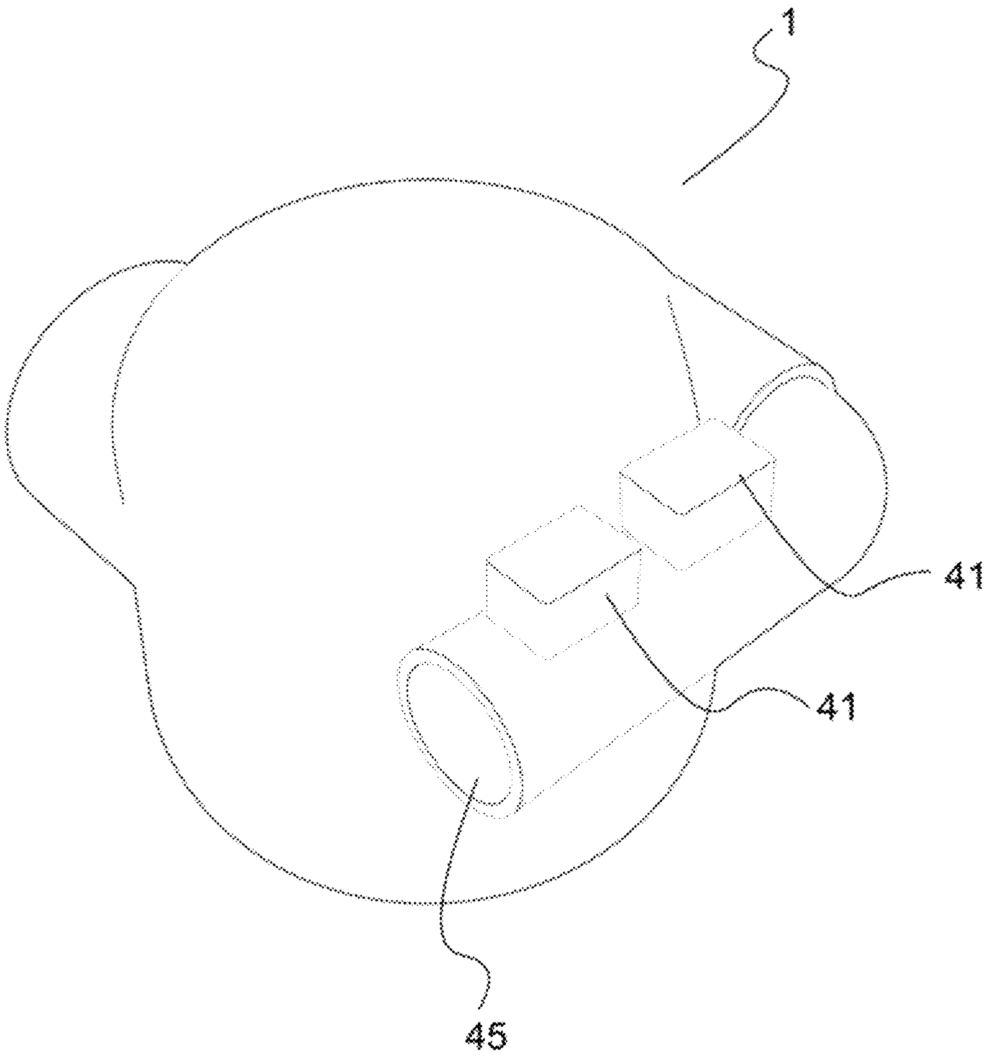
FIG. 19 is a schematic diagram showing multiple containment chambers in another form of the gas passage of a respiratory device in accordance with one embodiment.

The gas passage 4 of the respiratory device 1 includes walls 44 with an air intake 45 and an air outlet 46, which are configured to form at least two chambers. The overall shape of the gas passage 4 can be cubic, cylindrical, or other shapes which facilitate the flow of gas. The cross-sections of the air intake 45 and air outlet 46 of the walls 44 can be circular, elliptical, square, etc., and the air intake 45 and air outlet 46 may take the form of an opening or be defined as channels with height. The centerlines of the air intake 45 and the air outlet 46 of the walls 44 can be at any angle to each other. The materials of the walls 44 can include rigid materials such as polypropylene, polycarbonate, polyethylene terephthalate-1,4-cyclohexane dimethanol ester, polyamide, polyetheretherketone, or flexible materials like silicone, rubber, thermoplastic elastomer, thermoplastic polyurethane, fluororubber, and other materials like metal. At least one of the chambers formed by the walls 44 is the containment chamber 41, and the other chambers are flow chambers 43. When the respiratory device 1 is in use, the breathable gas substantially does not pass through the containment chamber 41-"substantially" being specifically defined here as the airflow through at least one containment chamber 41 accounting for at most 20% of the total airflow through the respiratory device 1. As shown in FIGS. 10A and 10B, the containment chamber 41 can be cubic, spherical, elliptical, or other shapes, with a total volume not exceeding half the overall volume of gas passage 4 and no less than 785 $mm^2$ (i.e., the volume of a cylinder with a diameter of at least 10 mm and a height of at least 10 mm). At least one wall 412 of the containment chamber 41 includes at least one through-opening 411. In other embodiments, a single wall 412 might have one or multiple through-openings 411, or different walls 412 might each have multiple through-openings 411. Each opening 411 has a minimum area of 0.19625 $mm^2$ (i.e., the area of the opening 411 when the opening 411 is a circular hole with a diameter of 0.5 mm). The shape of the openings 411 can be circular, elliptical, square, triangular, etc., preferably, the opening 411 is circular. Aside from the walls 412 with the opening 411, other walls 412 of the containment chamber 41 are closed, ensuring that noise sound waves enter the containment chamber 41 through the opening 411 and resonate with walls 412, which then dissipate the sound energy, thereby reducing noise levels without the sound waves rebounding back through the opening 411. The form of the wall 412 of the containment chamber 41 can be flat or curved and the wall 412 has a minimum thickness of 0.4 mm. The containment chamber 41 is typically placed at noise concentration areas, such as at the air intake 45 of the gas passage 4 or the inlet 331 of the blower 3, and can be external or internal to the flow chamber 43. The flow chamber 43 is configured to allow the flow of breathable gas and includes a connecting structure 431 to connect to the containment chamber 41. The connecting structure 431 can be an opening, a protrusion, a groove, a snap-fit, or a non-removable connection such as adhesive or integral molding. The blower 3 is provided within the flow chamber 43 and is fixed to the gas passage 4 through connectors that can be plastic parts with damping structures or flexible materials such as silicone, rubber, thermoplastic elastomer, thermoplastic polyurethane, or fluororubber. Moreover, the opening 411 of the containment chamber 41 communicates with the flow chamber 43 through a neck 5. The neck 5 has a first end 51 to connect to the containment chamber 41 and a second end 52 to connect to the flow chamber 43. Specifically, the first end 51 of the neck 5 connects to the opening 411 of the containment chamber 41, while the second end 52 connects to the connecting structure 431 of the flow chamber 43. In such a way, the containment chamber 41, the neck 5, and flow chamber 43 together form a complete gas passage 4. In other embodiments, the neck 5 is integrally formed with the containment chamber 41 and the flow chamber 43. As shown in FIG. 15A, the neck 5 is typically a straight channel with a certain height, with the height of the neck 5 being at least 0.4 mm (as shown in FIG. 15B, in other embodiments, the neck 5 is just an opening 411 with the wall thickness, and the thickness of the wall 412 of the containment chamber 41 is at least 0.4 mm; in another embodiment, the neck 5 is a curved channel). The ratio of the height of the neck 5 to the height of the containment chamber 41 is at least 1:300. The height of the neck 5 is preferably 1/17 to ⅓ of the height of the containment chamber 41. The parallel cross-sections from the first end 51 to the second end 52 of the neck 5 are identical (including but not limited to the same shape and size). The maximum cross-section of the neck 5 can be circular, elliptical, square, diamond-shaped, or other regular or irregular shapes (i.e., shapes that cannot be defined, named). The cross-section of the neck 5 is preferrably circular, and the neck 5 is a circle with a diameter of at least 0.5 mm. The surface area of the containment chamber 41 is at most 1000 times the cross-sectional area of the neck 5. The neck 5 is configured solely to communicate with the chambers and to allow minimal or no airflow (i.e., the airflow through the neck 5 accounts for at most 20% of the total airflow through the respiratory device 1). Therefore, the direction of the centerline of the neck 5 is set, and the airflow path in the flow chamber 43 is set to form a main airflow path, and the angle between the tangent direction of the main airflow path at the connecting structure 431 of the flow chamber 43 and the centerline of the neck 5 is greater than or equal to 30°, as shown in FIG. 13A. Typically, the centerline of the inlet 331 of the blower 3 is parallel to the centerline of the neck 5 (as shown in FIGS. 13B and 13C, in other embodiments, the two centerlines can be at any angle to each other). In some types of the gas passage 4, where noise control is reasonably managed, the gas passage 4 is set to only have the containment chamber for noise reduction. In some other cases, the flow chamber 43 includes noise reduction components that work in conjunction with the containment chamber 41 to further reduce noise; for example, multiple walls spaced at intervals can be provided within the flow chamber 43 to perform noise reduction on the airflow entering the flow chamber 43.

Figure 20A:
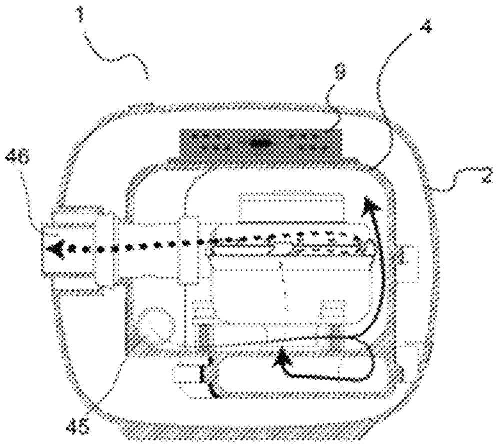
FIGS. 20A and 20B are schematic diagrams showing different materials between the casing and the gas passage of a respiratory device in accordance with one embodiment.
Figure 20B:
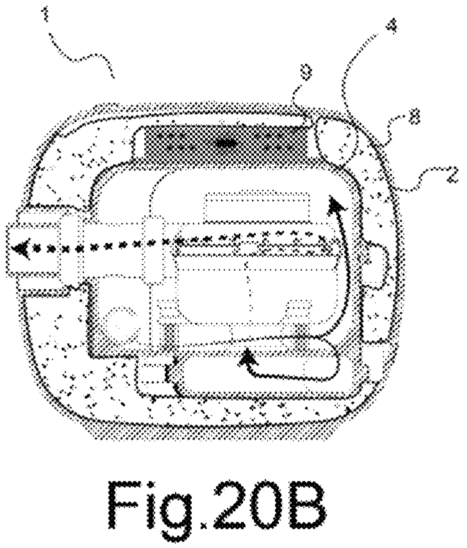

The casing 2 is configured to house the gas passage 4. The specific form of the casing 2 is determined based on the structure of the internal gas passage 4. The casing 2 has a first opening 21 and a second opening 22, with the first opening 21 configured to allow airflow in and the second opening 22 configured to allow airflow out. The material of the casing 2 can include one or more of the following: rigid materials such as polypropylene, polycarbonate, polyethylene terephthalate-1,4-cyclohexane dimethanol ester, polyamide, polyetheretherketone, or flexible materials such as silicone, rubber, thermoplastic elastomer, thermoplastic polyurethane, fluororubber, or other materials like metals. As shown in FIG. 20B, in other embodiments, soundproofing material 7, silicone, or other flexible buffers with good vibration absorption or dispersion properties are placed between the casing 2 and the gas passage 4. In some embodiments, as shown in FIG. 20A, there is a certain distance between the casing 2 and the gas passage 4, while in others, the casing 2 and the gas passage 4 are closely fitted.

The electronic assembly 9 is provided between the casing 2 and the gas passage 4 and includes components such as printed circuit boards, power sources, signal indicators, and screens.

Figure 2:
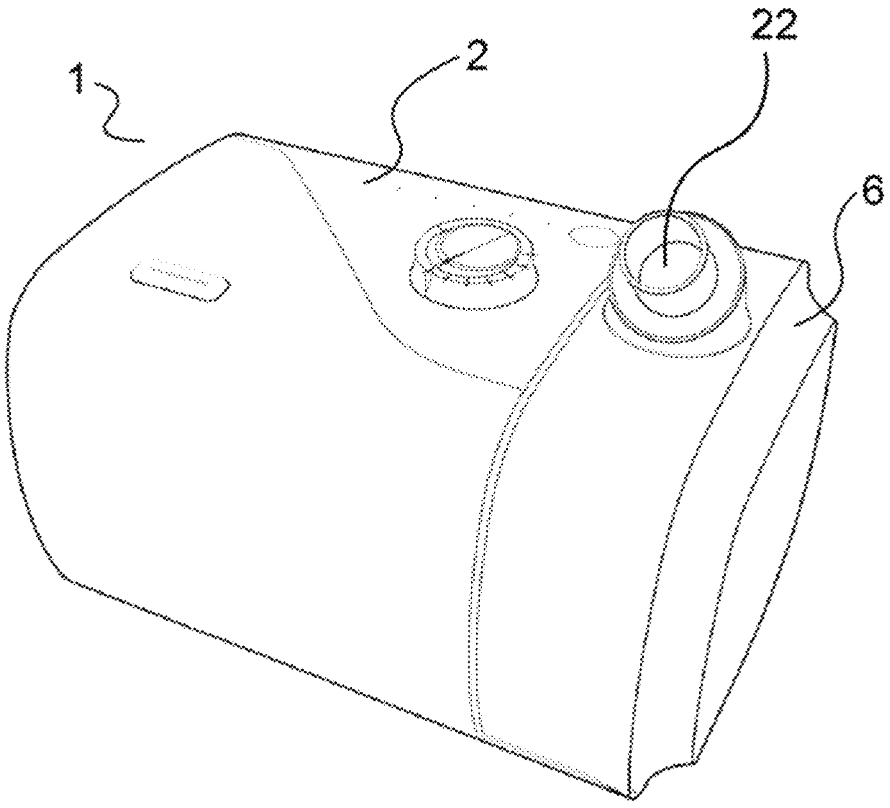
FIG. 2 is a three-dimensional schematic diagram of a respiratory device with a water tank in accordance with one embodiment.
Figure 3:
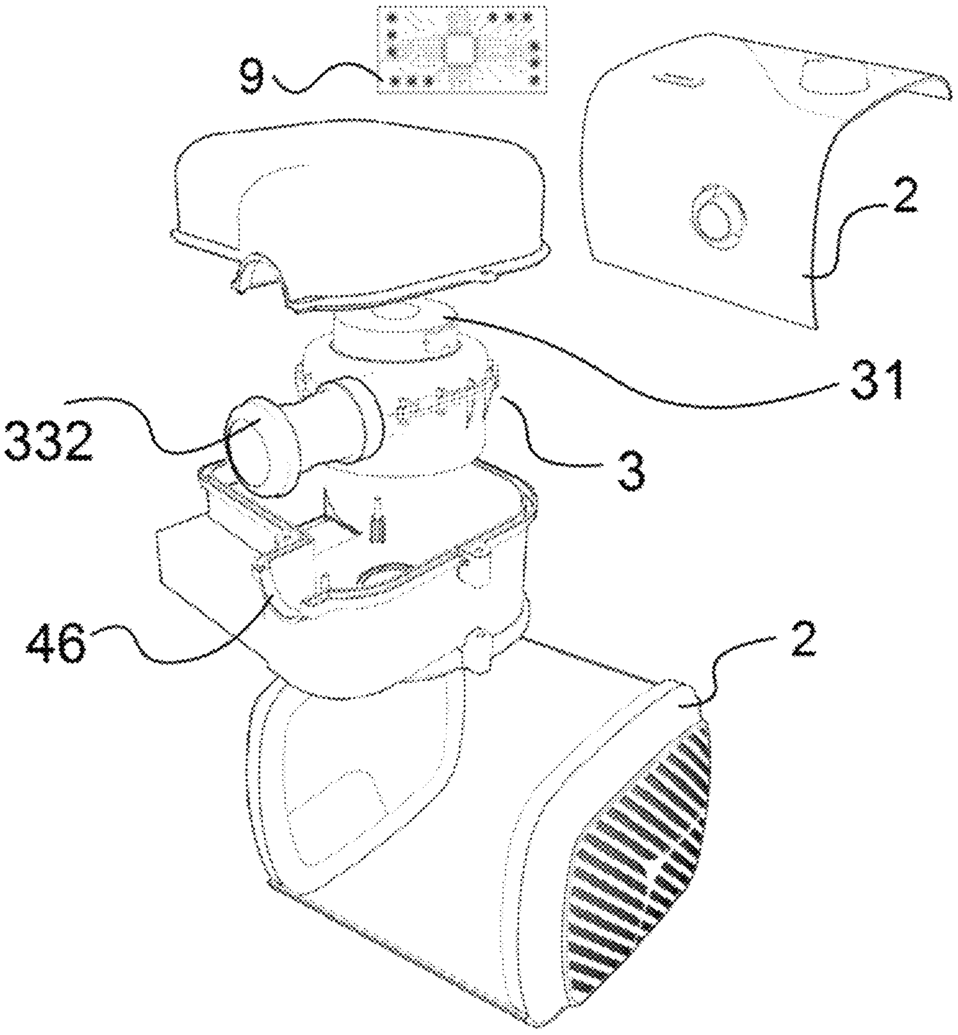
FIG. 3 is an exploded schematic diagram of a respiratory device in accordance with one embodiment.
Figure 4:
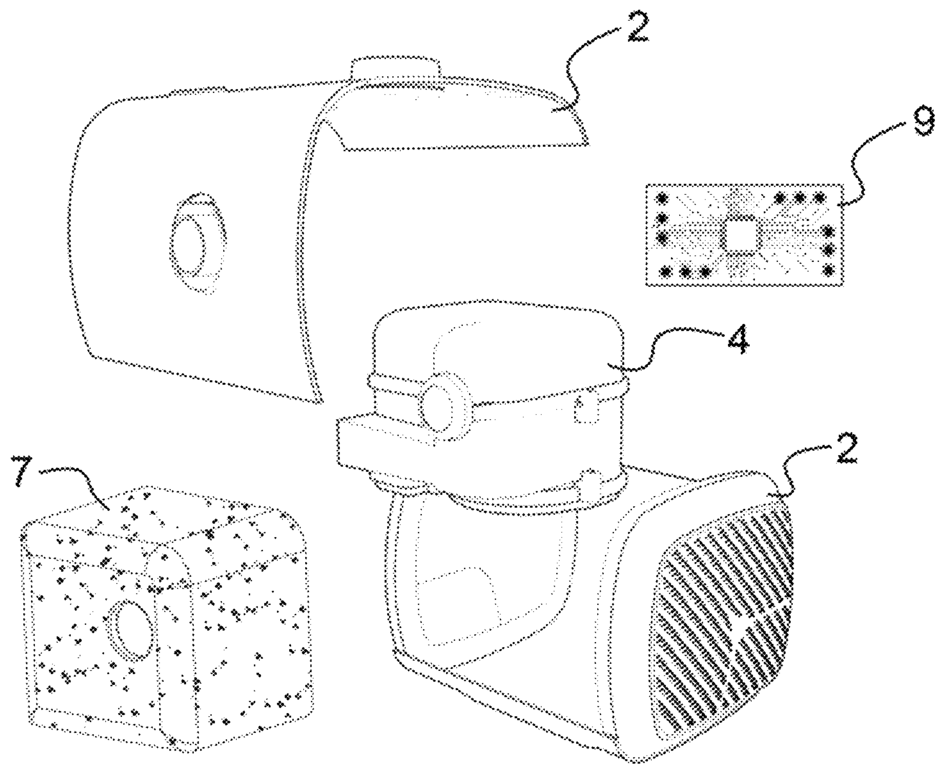
FIG. 4 is an exploded schematic diagram of a respiratory device with soundproofing materials in accordance with one embodiment.
Figure 5:
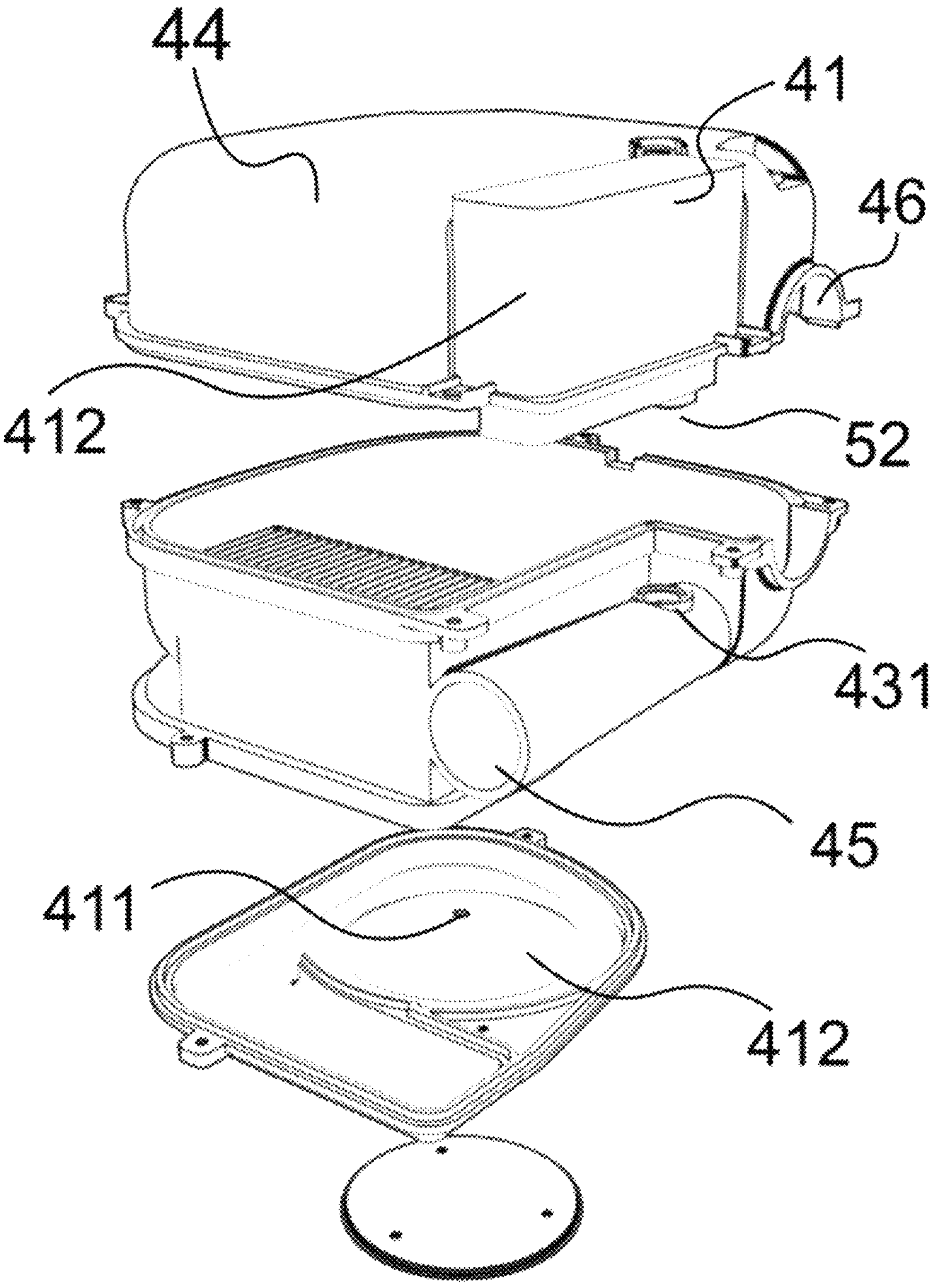
FIG. 5 is a three-dimensional schematic diagram of the gas passage of a respiratory device having multiple containment chambers in accordance with one embodiment.
Figure 6:
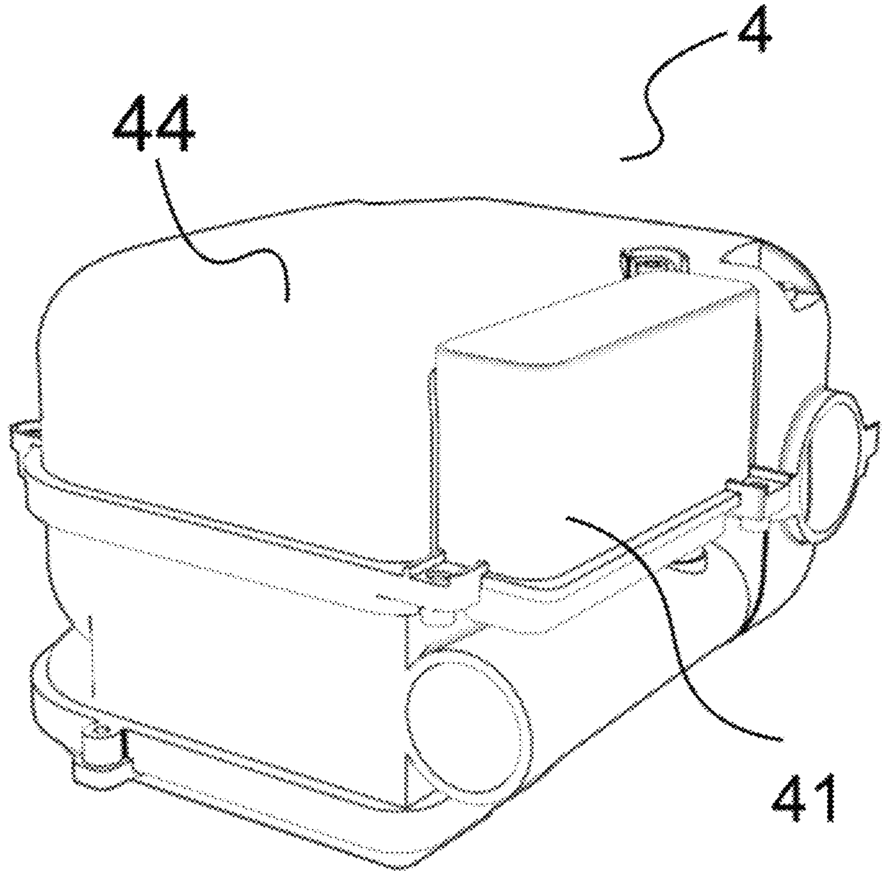
FIG. 6 is a three-dimensional schematic diagram of the gas passage of a respiratory device with an external containment chamber in accordance with one embodiment.
Figure 7:
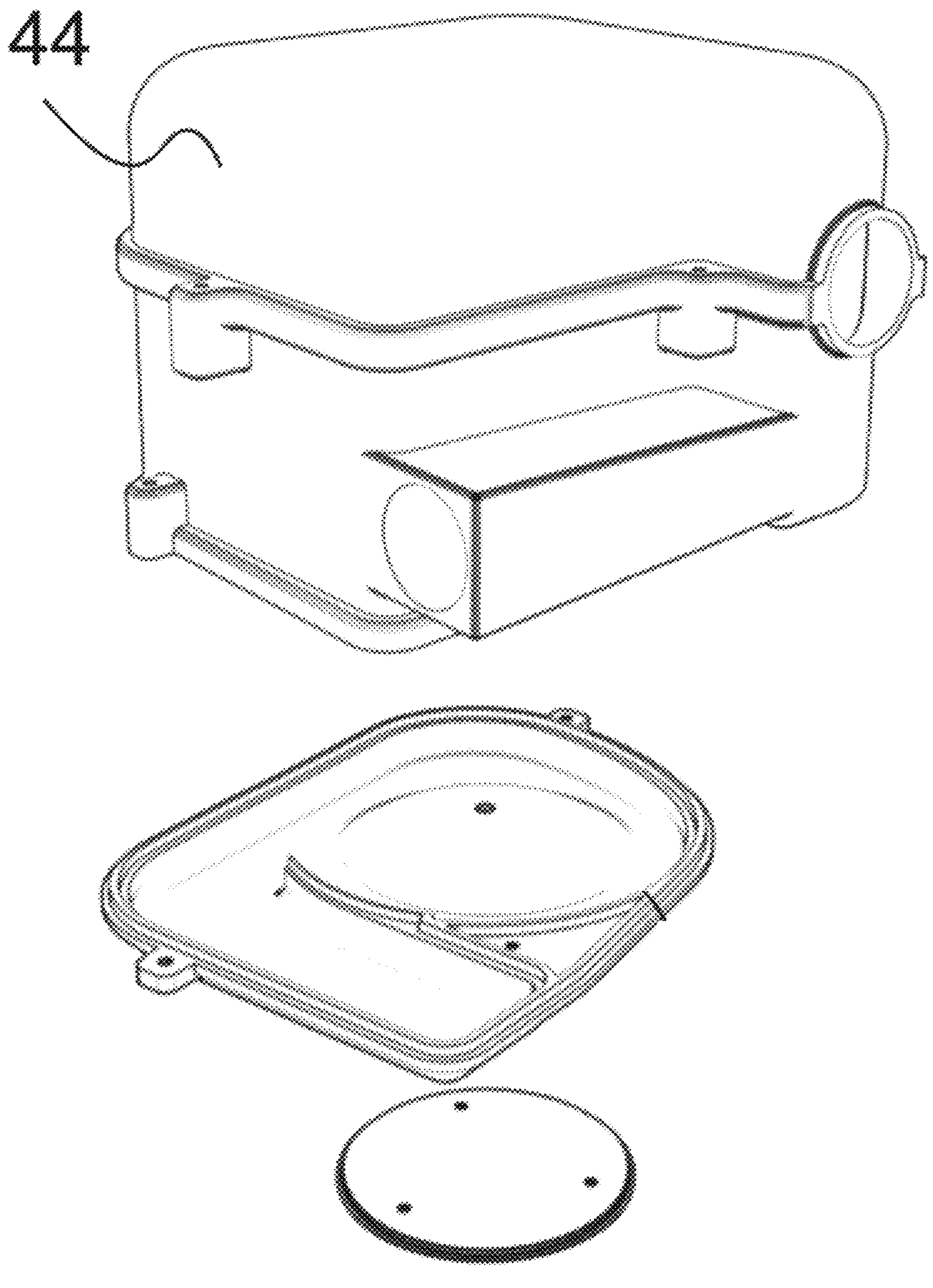
FIG. 7 is a three-dimensional schematic diagram of the gas passage of a respiratory device with an internal containment chamber in accordance with one embodiment.
Figure 8:
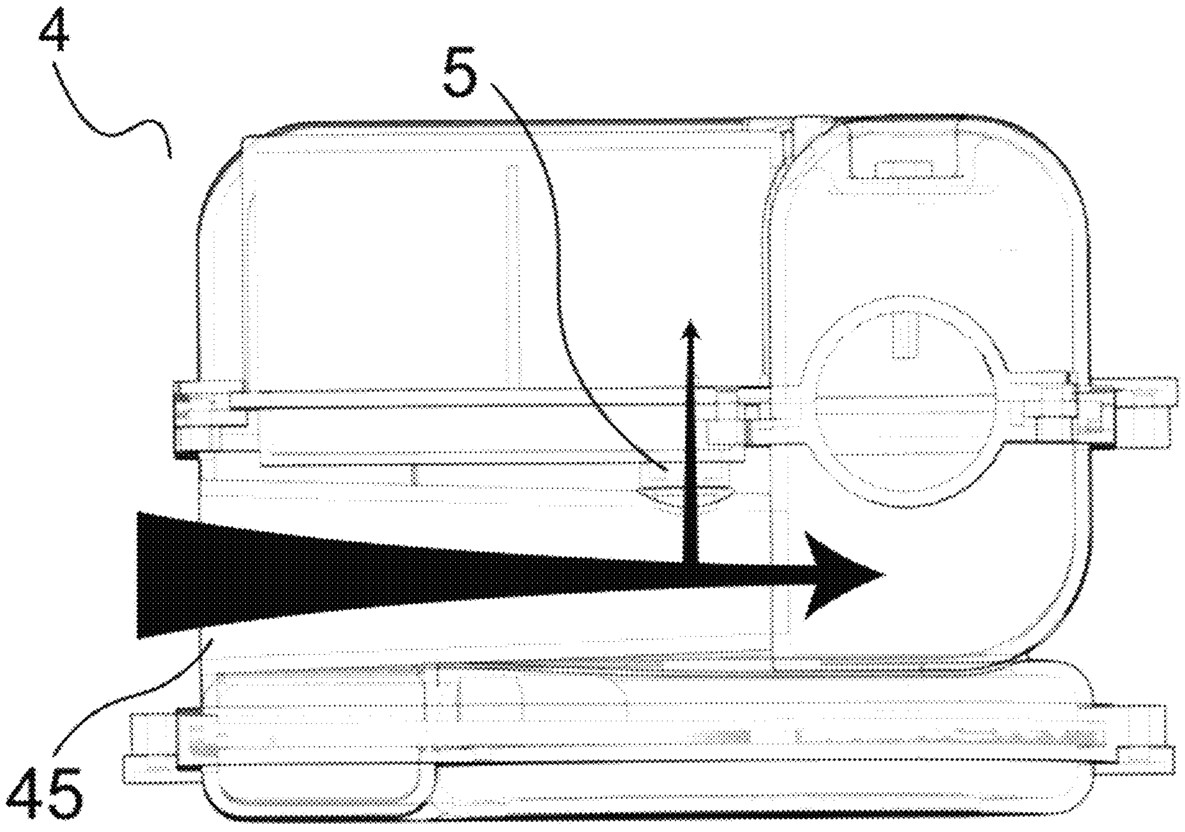
FIG. 8 is a schematic diagram of the airflow path in the gas passage of a respiratory device in accordance with one embodiment.
Figure 9:
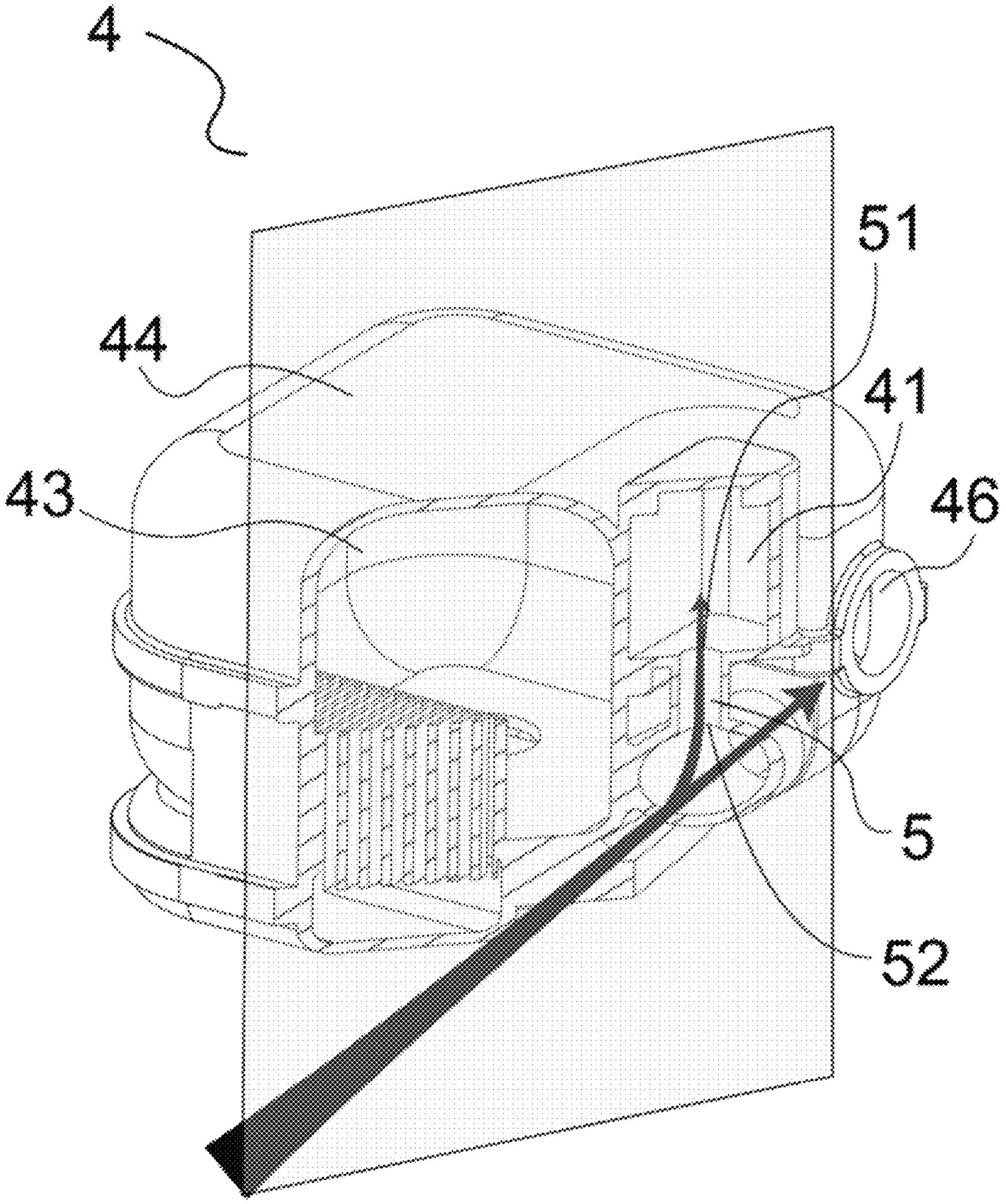
FIG. 9 is a three-dimensional cross-sectional schematic diagram of the containment chamber in the gas passage of a respiratory device in accordance with one embodiment.

In other embodiments, as shown in FIG. 2, the respiratory device 1 includes a blower 3, a gas passage 4, a water tank 6, and a casing 2. The water tank 6 can be made from one or more of the following materials: rigid materials including polypropylene, polycarbonate, polyethylene terephthalate-1,4-cyclohexane dimethanol ester, polyamide, polyetheretherketone, or flexible materials like silicone, rubber, thermoplastic elastomer, thermoplastic polyurethane, and fluororubber. In some embodiments, the water tank 6 can take in a portable, foldable form.

In other embodiments, as shown in FIG. 2, the respiratory device 1 includes a blower 3, a gas passage 4, a water tank 6, and a casing 2. The casing 2 is configured to house the gas passage 4, with its specific form determined by the structure of the internal gas passage 4. The casing 2 has a first opening 21, configured to allow airflow in, and the water tank 6 has a second opening 22, configured to allow airflow out.

In other embodiments, as shown in FIGS. 11, 12, 22, and 23, the gas passage 4 of the respiratory device 1 shares a wall with the casing 2, meaning the inner wall of the casing 2 forms the gas passage 4. In other embodiments, the gas passage 4 of the respiratory device 1 shares part of a wall with the casing 2, meaning part of the inner wall of the casing 2 and the wall of the gas passage 4 together form the airflow channel.

Embodiment 2

This disclosure relates to a respiratory device 1 with a containment chamber 41, configured to deliver pressurized breathable gas to a patient's airway. The respiratory device 1 includes a blower 3 that continuously generates a positive pressure airflow, a gas passage 4 that regulates and directs the gas, and a casing 2 that houses the gas passage 4 (in another embodiment, the respiratory device 1 includes a blower 3, a gas passage 4, a water tank 6, and a casing 2).

The difference between this embodiment and Embodiment 1 is that the gas passage 4 includes two containment chambers 41, one of which is externally connected to the air intake 45 of the gas passage 4 through a neck 5, and the other containment chamber 41 is built into the flow chamber 43. As shown in FIG. 13B, specifically, the containment chamber 41 has an opening 411 and connects to the connecting structure 431 of the flow chamber 43 through a neck 5. The centerline of the neck 5 forms a 90° angle with the main airflow path at the connecting structure 431 of the flow chamber 43, and the airflow through a single containment chamber accounts for no more than 3% of the total airflow of the respiratory device 1. In this embodiment, the containment chamber 41 captures sound waves at the air intake 45 of the gas passage 4 and provides multi-faceted walls 412 that resonate with the sound waves, converting sound energy into kinetic energy for dissipation. The blower 3 is provided within the flow chamber 43, and the inlet 331 of the blower 3 connects to the flow chamber 43. The containment chamber 41 is provided within the flow chamber 43 and has an opening 411 coaxial with the inlet 331 of the blower 3, and the opening 411 faces the inlet 331 of the blower 3. When the respiratory device 1 is in operation, the high-speed airflow generated by the blower 3 creates a negative pressure in the containment chamber 41, slowing the propagation speed of noise entering the chamber, reducing the likelihood of sound rebounding, and dissipating the remaining noise in the containment chamber 41 through vibration of the walls 412. The overall noise of the gas passage 4 is filtered twice by the containment chamber 41 to achieve a quieter operation.

In another embodiment, the respiratory device 1 may include multiple blowers 3, and the number of flow chambers 43 and containment chambers 41 can be adjusted accordingly to achieve optimal noise levels.

Embodiment 3

This disclosure pertains to a respiratory device 1 with a containment chamber 41, configured to deliver pressurized breathable gas to a patient's airway. The respiratory device 1 includes a blower 3 that continuously generates a positive pressure airflow, a gas passage 4 that regulates and directs the gas, and a casing 2 that houses the gas passage 4 (in another embodiment, the respiratory device 1 includes a blower 3, a gas passage 4, a water tank 6, and a casing 2).

Figure 21:
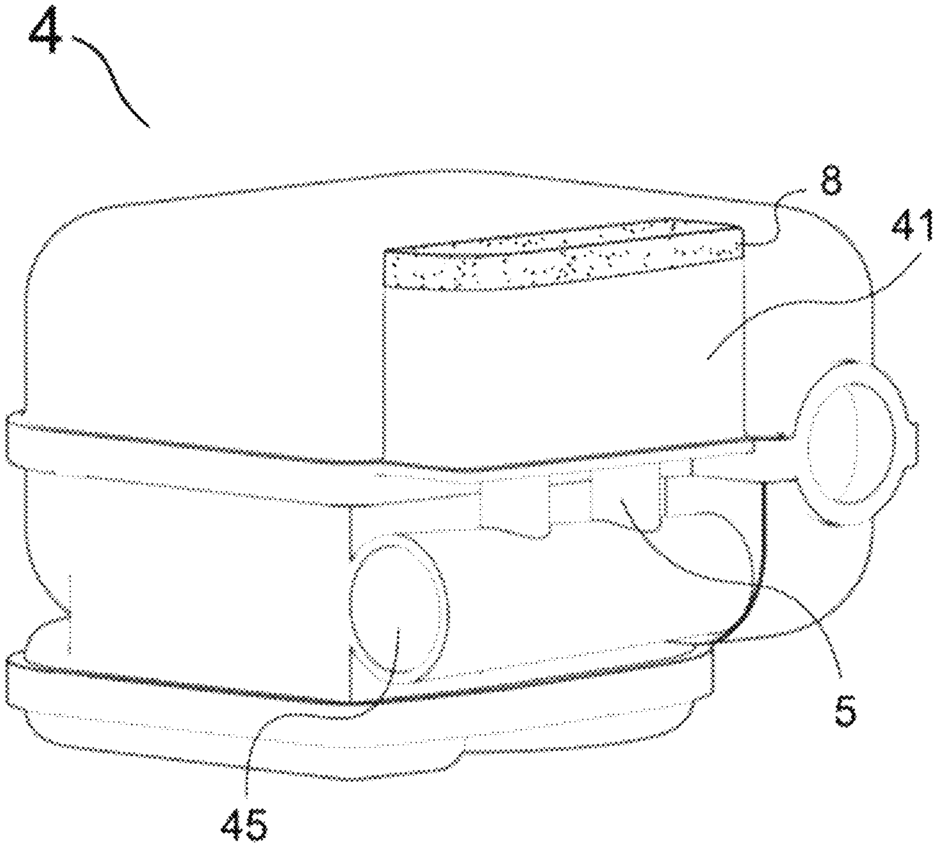
FIG. 21 is a schematic diagram of the gas passage with containment chambers made of different materials in a respiratory device in accordance with one embodiment.
Figure 22:
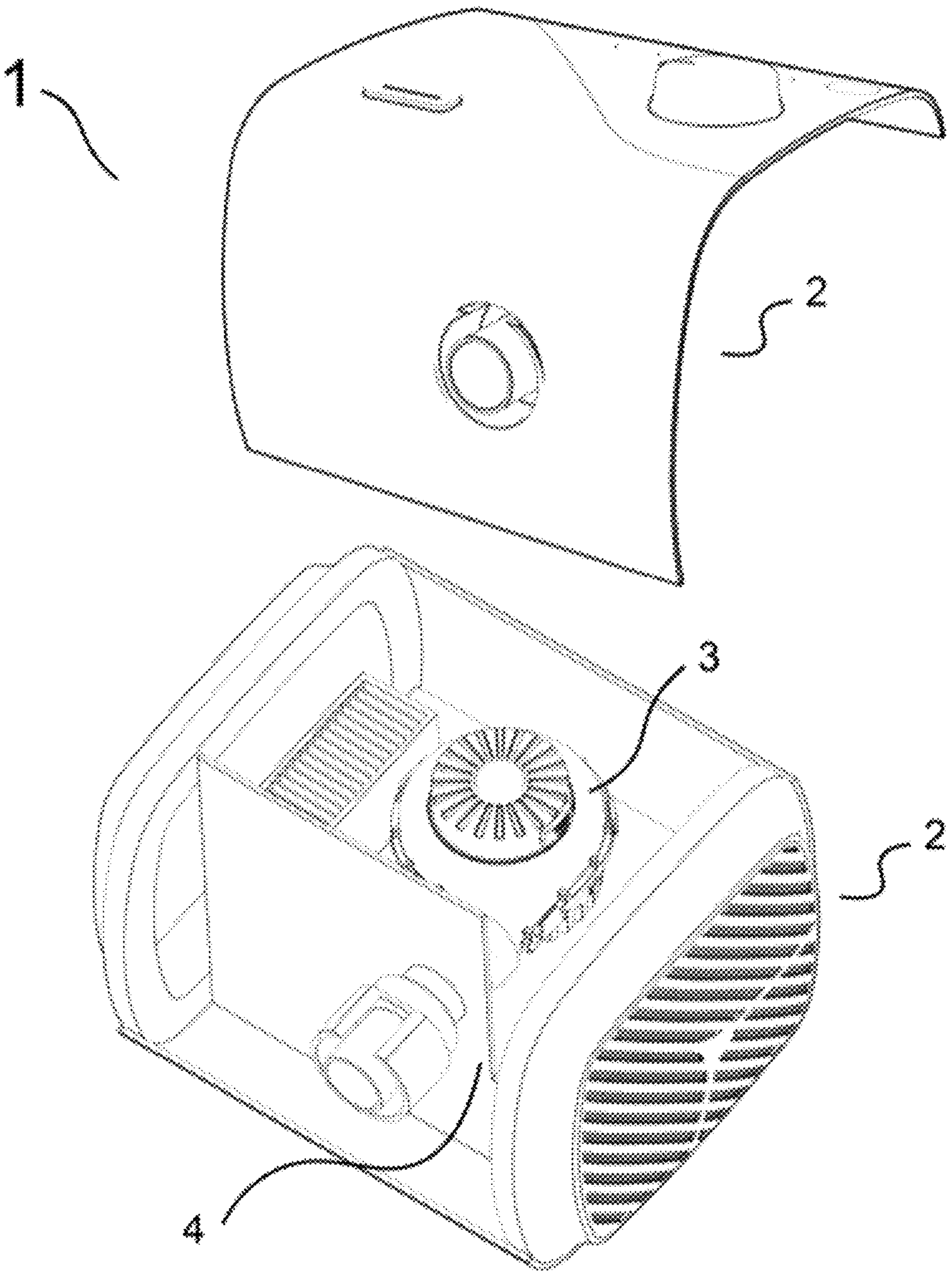
FIG. 22 is a schematic diagram showing the shared wall between the gas passage and the casing in a respiratory device in accordance with one embodiment.
Figure 23:
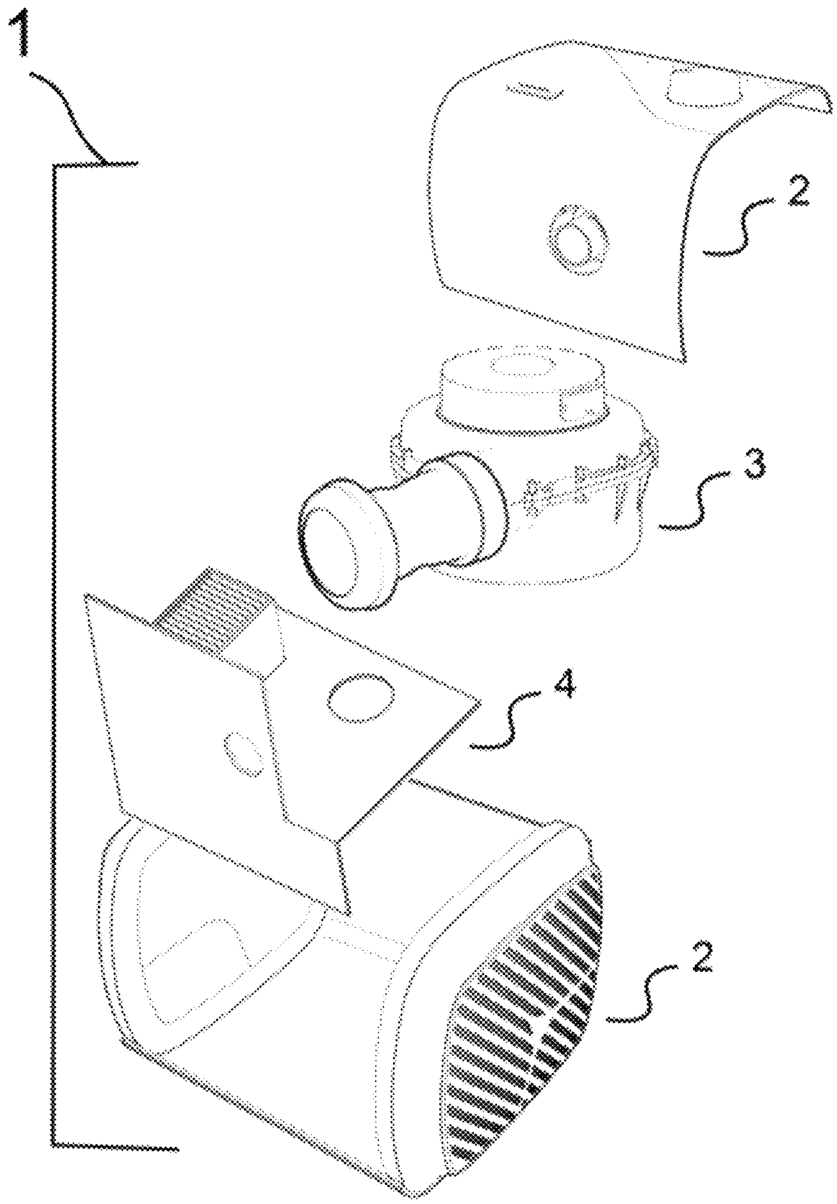
FIG. 23 is an exploded view showing the shared wall between the gas passage and the casing in a respiratory device in accordance with one embodiment.
Figure 24:
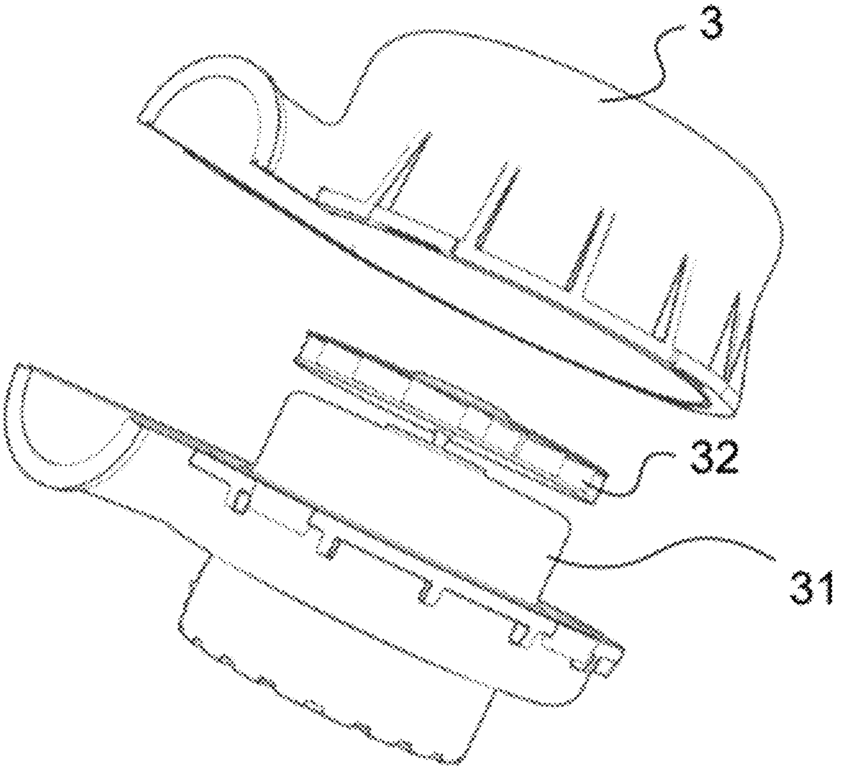
FIG. 24 is an exploded view of the blower in a respiratory device in accordance with one embodiment.

The distinction of this embodiment from Embodiment 1 lies in that the walls 412 of the containment chamber 41 include at least two different materials (such as soundproofing material 7 combined with plastic, or silicone plus plastic). As shown in FIG. 21, in this embodiment, the walls 412 of the containment chamber 41 include a rigid material, identical to the material of the walls 44 of the gas passage 4, and a first material 8, which is different from the rigid material. The rigid material serves as the foundational structure of the containment chamber 41 to ensure its stability and durability, while the first material 8 enhances the absorption, dissipation, or isolation of noise, further aiding the hard plastic in noise reduction. The first material 8 may be one of soundproofing material 7, silicone, rubber, thermoplastic elastomer, thermoplastic polyurethane, fluororubber, or any other material. This design considers the characteristics of different materials and their acoustical effects to achieve better noise reduction. In configurations where the walls 412 of the containment chamber 41 include the soundproofing material 7, the principle of noise reduction is primarily based on its porous structure and material properties, offering multiple acoustic impedances to absorb and disperse sound energy. As sound waves enter the soundproofing material 7, they undergo multiple reflections and refractions within the pores, and due to the inherent damping characteristics of the soundproofing material 7, this process efficiently converts sound energy into heat or mechanical energy, thereby reducing the energy of the sound waves, and consequently, reducing noise propagation and impact.

In other embodiments, where the walls 412 of the containment chamber 41 include silicone material, the high flexibility and moldability of silicone allow it to adapt to various complex surfaces and structures, effectively filling and covering the areas generating noise. Moreover, the minute vibrations of silicone molecules under the influence of sound waves consume the sound energy, thus achieving noise reduction.

Furthermore, the design of the containment chamber 41 with multiple materials not only improves the noise reduction level of the gas passage 4 to some extent but also provides greater flexibility for future optimizations and modifications of the gas passage 4. This allows for adjustments based on specific application needs and acoustical performance, enabling more effective noise reduction within specific frequency ranges.

The implementation of a respiratory device assembly at least includes the following benefits:

1. The containment chamber provided by this disclosure effectively reduces the noise of the device. a. Location: In use, respiratory devices encounter noise due to the opposing directions of the exhaled air from the user and the airflow generated by the blower, or when part of the airflow collides with and changes direction upon hitting the walls of the gas passage, causing some noise to flow out through the air inlet of the gas passage. To mitigate such noise, based on the principles of sound fluctuation and propagation, containment chambers are added at noise concentration areas such as the air intake of the gas passage and the inlet of the blower. These chambers capture and dissipate noise through vibration. Depending on the placement of the containment chamber and applying aerodynamic principles, different noise reduction effects can be achieved. For example, a containment chamber provided at the blower inlet leverages the principle of negative pressure in aerodynamics. The high-speed airflow at the opening creates negative pressure inside the containment chamber, slowing down the noise propagation due to reduced transmission medium, decreasing the likelihood of sound reflection and allowing the noise retained in the containment chamber to dissipate through vibrations against the chamber walls. b. Principle: While the wall of the containment chamber connected to the neck includes an opening, the other walls of the containment chamber are closed (i.e., without openings), and the area of the opening is proportionate to the surface area of the containment chamber, effectively reducing noise escape from the opening. The centerline of the neck is oriented at an angle greater than 30° relative to the main airflow path to ensure noise enters the containment chamber while preventing excessive airflow from entering, allowing the noise within the containment chamber to convert sound energy into kinetic energy through vibration. c. Material: The primary function of the containment chamber is to convert sound energy into other forms of energy. The containment chamber includes rigid materials that resonate with the noise's sound waves against the walls of the containment chamber, thus converting sound energy into kinetic energy to silence the noise. Alternatively, the containment chamber can include materials such as silicone, where the noise's sound waves, passing through these materials, are converted into thermal energy through friction and vibration, thereby reducing or eliminating noise.

2. The containment chamber can replace the soundproofing materials in respiratory devices, enhancing the safety of the devices. The design of a gas passage without soundproofing materials improves the safety of the devices. In 2021, a renowned international brand issued its first global recall notice involving some of its BiPAP devices, CPAP devices, and mechanical ventilators, followed by several more recalls. The recalls were primarily due to the use of sound-dampening materials within the gas passages of the ventilators, which could release particles and volatile organic compounds. The FDA received numerous complaints about this brand's CPAP and BiPAP ventilators. This incident not only had a negative impact on the brand but also affected millions of its users. Ventilators must achieve a noise level of 30 dB or less for marketing approval in FDA's regulations, and using soundproofing materials for noise reduction is currently the simplest method. Soundproofing materials, due to their unique porous structure and material properties, can convert noise into small amounts of energy to achieve effective noise reduction. Placing soundproofing materials inside the gas passage is the simplest and most common way to meet regulatory noise levels. However, soundproofing materials can easily cause health problems for several reasons: a. Soundproofing materials are typically made from synthetic materials such as polyurethane and polyether, which often contain various chemical additives or components. During the use of the device, these additives or components may gradually be released and turn into harmful substances that are detrimental to human health. Prolonged inhalation of these substances can negatively impact respiratory health and overall well-being. b. Soundproofing materials are often hygroscopic, which can be problematic in the humid environments created by ventilators during operation. These materials absorb moisture from the air, creating ideal conditions for the growth of bacteria and mold. Additionally, some ventilators provide humidification systems to enhance patient comfort, further promoting moisture absorption in the soundproofing materials within the internal environment.

c. When the gas passage is in operation, airflow moves through the soundproofing materials, causing friction and vibration. This can lead to the deterioration of the material surface and the release of tiny particles. The hygroscopic nature of the soundproofing materials not only fosters bacterial or fungal growth but can also lead to the decomposition of the material itself, generating small particles. These particles can ultimately be inhaled into the patient's respiratory system, posing significant health risks. Some patients may also have allergic reactions to these materials, potentially leading to respiratory allergic reactions or asthma attacks, thereby impacting respiratory health. These factors typically shorten the lifespan of soundproofing materials, necessitating frequent replacement to maintain their effectiveness in the gas passage. Alternatively, further research and development to enhance the physical and chemical stability of these materials can be pursued, though this would increase the costs associated with usage and production.

The noise reduction structure provided by this disclosure can achieve regulatory noise levels within the gas passage with reduced use of soundproofing materials, thus enhancing both the safety and the lifespan of the device, as well as aligning with environmental sustainability principles compared with the existing ventilator's design with foam within the gas passage. The noise reduction structure provided by this disclosure incorporates a series of improvements and uses multiple effective noise-reducing structures, supported by theoretical and experimental data. The resulting gas passage significantly reduces noise, meeting regulatory noise levels without the use of soundproofing materials. The advantages of reducing soundproofing materials in the gas passage at least include: a. Placing soundproofing materials within the gas passage is the most straightforward and common method to achieve regulatory noise levels in devices related to respiratory care. However, particles from the decomposition of these materials, if inhaled, are usually harmful to human health, particularly for those requiring long-term and prolonged use of ventilators. b. Soundproofing materials degrade and damage quickly compared to plastic materials and are among the shortest-lived components used within the gas passage. The lifespan of gas passages containing soundproofing materials is reduced due to the presence of these materials. This disclosure allows patients to opt for a gas passage with reduced soundproofing materials, thereby enhancing the overall lifespan of the ventilator. Additionally, the absence of soundproofing materials means a simpler internal structure of the gas passage, eliminating the need for extra fixtures to secure these materials, reducing mechanical wear and maintenance requirements, and improving the device's reliability and stability. c. While soundproofing materials are a common means of noise reduction in ventilators and effectively lower noise levels, their manufacture, use, and disposal have environmental impacts. Firstly, as synthetic materials, their production requires significant energy and resources, and may involve the use of chemicals that contribute to pollution. Besides, high-quality noise-reducing soundproofing materials are generally costly, reducing health risks but also increasing the purchase costs of the devices. Designs that reduce soundproofing materials within the gas passage avoid these issues. They not only lessen the environmental impact but also reduce waste production and save costs associated with purchasing these materials. d. Gas passages with reduced soundproofing materials which meet regulatory noise levels provide patients with more flexible options. Patients can choose between gas passages with or without soundproofing materials. Those with higher requirements for quietness may opt for passages with soundproofing materials to achieve lower noise levels and improve sleep quality. Alternatively, adding health-friendly materials like silicone or rubber within the gas passage can also reduce noise while eliminating the impacts of soundproofing materials. Compared to soundproofing materials, silicone and plastics usually offer better durability, corrosion resistance, and resilience, are less affected by environmental conditions, and have better chemical stability, making them less susceptible to chemical influences and thus longer-lasting.

By utilizing effective noise reduction structures such as the containment chamber, the respiratory device can achieve the regulatory or even lower noise levels without relying on materials prone to decomposition or degradation, ensuring greater stability. This disclosure uses multiple structures that effectively reduce noise, offering an alternative to traditional gas passages that utilize soundproofing materials. Specifically, the various noise reduction structures employed in this disclosure include, but are not limited to, the containment chamber, the conical inlet tube, more strategically placed and positioned blowers, arc-shaped walls that are essentially coaxial with the inlet of the blower intake, and inner walls with rounded contours of the gas passage that are positioned opposite the airflow path. The use of these structures and components not only lowers the noise level of the device but, more importantly, the noise-reducing components within the gas passage and the internal structure of the gas passage itself, as well as the positional relationships among various structures, are all based on ample existing and experimental data supported by scientific analysis. This ensures the scientific validity and credibility of the design of the gas passage, which makes the gas passage's performance more reliable and stable. This gas passage design not only improves the performance of the product but also provides patients with a quieter and more reliable user experience.

3. The structural design of the containment chamber enhances the device's reliability and extends its operational lifespan. The gas passage design, free from materials prone to decomposition or degradation, utilizes physically and chemically stable structures to prolong the device's lifespan, ensuring longer-lasting use. Additionally, the design eliminates the need for easily degradable materials, simplifying the internal structure of the gas passage. This obviates the need for extra components to secure special materials, reducing the variety of production components and thereby lowering the complexity of manufacturing and assembly. This contributes to the device's enhanced reliability and stability. Furthermore, soundproofing materials often require timely replacement and cleaning to ensure health safety, and those placed within devices are typically non-replaceable and non-cleanable. The design without soundproofing materials avoids these maintenance steps, reducing the upkeep required for the internal soundproofing materials of the gas passage and bringing convenience to the maintenance of the device. These aspects make respiratory devices provided by this disclosure more competitive on the market, making them more readily accepted.

4. By employing simpler structures and materials, the respiratory device provided by this disclosure reduces the cost while being environmentally friendly. The gas passage in this disclosure avoids traditional soundproofing materials, thereby reducing the additional costs associated with purchasing and manufacturing soundproofing materials. The gas passage in this disclosure only has plastic parts for the casing of the gas passage and as the material forming the chambers and gas passage, and it uses silicone materials in connectors to secure the blower to the casing of the gas passage. Compared to the more complex structures in the market that include soundproofing materials within the respiratory device's gas passage, this design, composed of only two types of materials, is easier to process and assemble. This simplification makes the manufacturing process more straightforward and efficient, saving substantial time and labor resources. Furthermore, high-quality noise-reducing materials are typically expensive, adding extra cost burdens. In contrast, the design without soundproofing materials lowers these costs. Additionally, reducing the use of auxiliary materials like soundproofing materials also lessens environmental impact, aligning with modern societal demands for environmental sustainability and contributing positively to environmental protection. Soundproofing materials can release harmful chemicals during production and disposal, causing environmental pollution. The gas passage design without these materials avoids the release of such harmful substances, minimizing negative environmental impacts. Therefore, this design, which does not use soundproofing materials or materials prone to decomposition or degradation and relies only on silicone and plastic, not only reduces the cost of the device but also is environmentally friendly, offering a more sustainable and economical solution.

The above description of the embodiments of the disclosure is provided with reference to the accompanying drawings. However, the disclosure is not limited to the specific embodiments described above. These specific embodiments are merely illustrative and not restrictive. Those skilled in the art, in light of the teachings of the disclosure, may make many modifications and variations without departing from the spirit and scope of the disclosure as defined by the claims. All such modifications and variations are within the protection scope of the disclosure.

It must be noted that as used herein and in the appended claims, the singular forms "a", "an", and "the" include their plural equivalents, unless the context clearly dictates otherwise.

The invention claimed is:

1. A respiratory device, configured to deliver pressurized breathable gas to an airway of a patient, the respiratory device comprising:
- at least one blower, comprising:
  - a motor with a rotor,
  - at least one impeller provided on the rotor, and
  - a housing with an inlet and an outlet,
  - wherein the at least one blower is configured to generate the pressurized breathable gas;
- a gas passage, comprising:
  - walls with an air intake and an air outlet,
    - wherein the walls are configured to form at least two chambers;
  - a casing, configured to house the gas passage;
  - an electronic assembly, provided between the casing and the gas passage;
    - wherein at least one of the at least two chambers is a containment chamber, comprising:
      - at least one wall with at least one through-opening to allow airflow between the containment chamber and at least one other of the at least two chambers; and
    - wherein, when the respiratory device is in use, no more than 20% of breathable gas that passes through the respiratory device passes through the containment chamber.

2. The respiratory device according to claim 1, wherein at least one of the two chambers other than the containment chamber is a flow chamber, and the at least one blower is provided on the flow chamber.

3. The respiratory device according to claim 1, wherein one or more of the at least one wall of the containment chamber is flat.

4. The respiratory device according to claim 1, wherein one or more of the at least one wall of the containment chamber is curved.

5. The respiratory device according to claim 1, wherein the at least one through-opening on the containment chamber takes a form of a circle with a diameter of at least 0.5 mm.

6. A respiratory device, configured to deliver pressurized breathable gas to an airway of a patient, the respiratory device comprising:
- at least one blower, comprising:
  - a motor with a rotor,
  - at least one impeller provided on the rotor, and
  - a housing with an inlet and an outlet,
  - wherein the at least one blower is configured to generate the pressurized breathable gas;
- a gas passage, comprising:
  - walls with an air intake and an air outlet,
    - wherein the walls are configured to form at least two chambers;
  - a casing, configured to house the gas passage,
  - an electronic assembly, provided between the casing and the gas passage;
    - wherein at least one of the at least two chambers is a containment chamber,
    - wherein at least one of the two chambers other than the containment chamber is a flow chamber,
    - wherein the containment chamber comprises at least one wall with at least one through-opening,
    - wherein, aside from the at least one wall with the at least one through-opening, other walls of the containment chamber are closed,
    - wherein the at least one through-opening of the containment chamber is to allow airflow between the containment chamber and the flow chamber through a neck, and
    - wherein, when the respiratory device is in use, no more than 20% of breathable gas that passes through the respiratory device passes through the containment chamber.

7. The respiratory device according to claim 6, wherein the at least one blower is provided within the flow chamber.

8. The respiratory device according to claim 6, wherein a height of the neck is at least 0.4 mm.

9. The respiratory device according to claim 6, wherein an area of the at least one through-opening on the containment chamber is at least 0.19625 $mm^2$.

10. A respiratory device, configured to deliver pressurized breathable gas to an airway of a patient, the respiratory device comprising:
- at least one blower, comprising:
  - a motor with a rotor,
  - at least one impeller provided on the rotor, and
  - a housing with an inlet and an outlet,
  - wherein the at least one blower is configured to generate the pressurized breathable gas;
- a gas passage, comprising:
  - walls with an air intake and an air outlet,
    - wherein the walls are configured to form at least two chambers;

a casing, configured to house the gas passage;

an electronic assembly, provided between the casing and the gas passage;

wherein at least one of the at least two chambers is a containment chamber, wherein at least one of the two chambers other than the containment chamber is a flow chamber, wherein the containment chamber comprises:

at least one wall with at least one through-opening;

wherein the at least one through-opening of the containment chamber is to allow airflow between the containment chamber and the flow chamber through a neck, wherein a maximum cross-sectional area of the neck is at least 0.19625 $mm^2$, wherein a height of the neck is at least equal to a thickness of the at least one wall of the containment chamber; and wherein, when the respiratory device is in use, no more than 20% of breathable gas that passes through the respiratory device passes through the containment chamber.

11. The respiratory device according to claim 10, wherein the gas passage comprises multiple containment chambers.

12. The respiratory device according to claim 10, wherein a ratio of the height of the neck to a height of the containment chamber is at least 1:300.

13. The respiratory device according to claim 10, wherein a maximum cross-section of the neck includes irregular shapes.

14. The respiratory device according to claim 10, wherein a wall thickness of the containment chamber is at least 0.4 mm.

15. A respiratory device, configured to deliver pressurized breathable gas to an airway of a patient, the respiratory device comprising:

at least one blower, comprising:

a motor with a rotor, at least one impeller provided on the rotor, and a housing with an inlet and an outlet, wherein the at least one blower is configured to generate the pressurized breathable gas;

a gas passage, comprising:

walls with an air intake and an air outlet, wherein the walls are configured to form at least two chambers;

a casing, configured to house the gas passage;

an electronic assembly, provided between the casing and the gas passage;

wherein at least one of the at least two chambers is a containment chamber, wherein at least one of the two chambers other than the containment chamber is a flow chamber, wherein the containment chamber comprises at least one wall with at least one through-opening with a neck to allow airflow between the containment chamber and the flow chamber; and wherein a total volume of the containment chamber is at least 785 $mm^2$.

16. The respiratory device according to claim 15, wherein the gas passage comprises multiple containment chambers.

17. The respiratory device according to claim 15, wherein the containment chamber receives airflow from the flow chamber through the neck.

18. The respiratory device according to claim 17, wherein a height of the neck is at least 0.4 mm.

19. The respiratory device according to claim 17, wherein a surface area of the containment chamber is at most 1000 times a cross-sectional area of the neck.

* * * * *